US011951164B2

United States Patent
Pisharodi

(10) Patent No.: US 11,951,164 B2
(45) Date of Patent: Apr. 9, 2024

(54) SYSTEMS AND METHODS FOR THE PREPARATION OF VACCINES UTILIZING PREDICTABLY INACTIVATED PATHOGENS

(71) Applicant: Madhavan Pisharodi, Brownsville,, TX (US)

(72) Inventor: Madhavan Pisharodi, Brownsville,, TX (US)

(73) Assignee: PERUMALA HOLDINGS, LLC, Brownsville, TX (US)

( * ) Notice: Subject to any disclaimer, the term of this patent is extended or adjusted under 35 U.S.C. 154(b) by 0 days.

(21) Appl. No.: 18/058,185

(22) Filed: Nov. 22, 2022

(65) Prior Publication Data

US 2023/0081767 A1   Mar. 16, 2023

Related U.S. Application Data

(63) Continuation-in-part of application No. 17/545,822, filed on Dec. 8, 2021, now Pat. No. 11,511,013.

(60) Provisional application No. 63/401,817, filed on Aug. 29, 2022, provisional application No. 63/359,381, filed on Jul. 8, 2022, provisional application No. 63/353,369, filed on Jun. 17, 2022, provisional application No. 63/233,697, filed on Aug. 16, 2021.

(51) Int. Cl.
*A61K 39/215* (2006.01)
*A61P 31/14* (2006.01)
*C07K 14/165* (2006.01)

(52) U.S. Cl.
CPC ............ *A61K 39/215* (2013.01); *A61P 31/14* (2018.01); *C07K 14/165* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

| | | |
|---|---|---|
| 3,721,072 A | 3/1973 | Miller |
| 3,773,044 A | 11/1973 | Wallace |
| 3,850,170 A | 11/1974 | Cox |
| 4,580,556 A | 4/1986 | Kondur |
| 4,742,760 A | 5/1988 | Horstman |
| 5,656,242 A | 8/1997 | Morrow et al. |
| 5,989,217 A | 11/1999 | Ohki et al. |
| 7,185,510 B2 | 3/2007 | Lee et al. |
| 8,336,821 B2 | 12/2012 | Shell et al. |
| 8,674,322 B2 | 3/2014 | Kohler |
| 11,052,169 B1 | 7/2021 | Pisharodi |
| 2006/0057020 A1 | 3/2006 | Tufo |
| 2006/0263276 A1 | 11/2006 | Pattee |
| 2008/0112845 A1 | 5/2008 | Dunn |
| 2008/0173178 A1 | 7/2008 | Metteer |
| 2010/0150793 A1 | 6/2010 | Chan |
| 2012/0128539 A1* | 5/2012 | Gross ............... F24F 8/192 422/121 |
| 2012/0211525 A1 | 8/2012 | Sadabadi |
| 2012/0301363 A1 | 11/2012 | Kim et al. |
| 2016/0001108 A1 | 1/2016 | Zhou et al. |
| 2017/0121701 A1 | 5/2017 | Dobrinsky et al. |
| 2017/0341762 A1 | 11/2017 | Breigenzer |
| 2018/0250430 A1 | 9/2018 | Machovina et al. |
| 2019/0009912 A1 | 1/2019 | Matsui |
| 2021/0299291 A1 | 9/2021 | Mullen et al. |

FOREIGN PATENT DOCUMENTS

DE    102021003829 A1    4/2022

OTHER PUBLICATIONS

Hankaniemi et al., Vaccine, vol. 37, Issue 40, pp. 5962-5971, (Year: 2019).*
Lo et al. (Scientific Reports 11:13804 (Year: 2021).*
Ong et al. (Heliyon 8 e11132 (Year: 2022).*
How a packaged system works' (Goodman) Jul. 29, 2016, [online] retrieved from <URL: https://web.archive.org/web/20160729193422/ https://www.goodmanmfg.com/resources/heating- cooling-101/how-a-packaged-system-works>.
'UV Inactivation of Rotavirus and Tulane Virus Targets Different Components of the Virions' (Araud) Feb. 3, 2020, [online] retrieved from <URL: https://doi.org/10.1128/AEM.02436-19.>.
'Irradiation of UVC LED at 277 nm inactivates coronaviruses in association to photodegradation of spike protein' (Ong) Oct. 17, 2022, [online] retrieved from <URL: https://doi.org/10.1016/j.heliyon.2022.e11132>.
'Ultraviolet A light effectively reduces bacteria and viruses including coronavirus' (Rezale) Jul. 16, 2020, [online] retrieved from <URL: https://doi.org/10.1371/journal.pone.0236199>.
'UVC-based photoinactivation as an efficient tool to control the transmission of coronaviruses' (Bhardwaj) Jun. 16, 2021, [online] retrieved from <URL: https://doi.org/10.1016/j.scitotenv.2021.148548>.
'UV C irradiation is highly efective in inactivating SARS CoV 2 replication' (Biasin) Mar. 18, 2021, [online] retrieved from <URL: https://doi.org/10.1038/s41598-021-85425-w>.
'UVC disinfects SARS CoV 2 by induction of viral genome damage without apparent effects on viral morphology and proteins' (Lo) Jul. 5, 2021, [online] retrieved from <URL: https://doi.org/10.1038/s41598-021-93231-7>.
Eischeid, Anne C. et al; "Molecular Indications of Protein Damage in Adenoviruses after UV Disinfection;" Applied and Environmental Microbiology, Feb. 2011, p. 1145-1147 vol. 77, No. 3.

(Continued)

*Primary Examiner* — Shanon A. Foley
*Assistant Examiner* — Myron G Hill
(74) *Attorney, Agent, or Firm* — D'Ambrosio & Menon, PLLC; Usha Menon

(57) ABSTRACT

A method is described for producing a vaccine from a neutered pathogenic source. The neutered pathogenic source may be a SARS-COV-2 virus that is neutered with a defined dose of UV-C light. The neutered SARS-COV-2 viral vaccine is administered through an inhalation pump.

13 Claims, 20 Drawing Sheets

(56) References Cited

OTHER PUBLICATIONS

Araud E, Fuzawa M, Shisler JL, Li J, Nguyen TH. 2020. UV inactivation of rotavirus and Tulane virus targets different components of the virions. Appl Environ Microbiol 86:e02436-19. https://doi.org/10.1128/AEM 02436-19.

Ma B, Gundy PM, Gerba CP, Sobsey MD, Linden KG. 2021. UV inactivation of SARSCoV-2 across the UVC spectrum: KrCl* excimer, mercury-vapor, and light-emitting-diode (LED) sources. Appl Environ Microbiol 87: e01532-21. https://doi.org/10.1128/AEM.01532-21.

Christin Scheller; "Physicochemical properties of SARS-CoV-2 for drug targeting, virus inactivation and attenuation, vaccine formulation and quality control" Electrophoresis 2020, 41, pp. 1137-1151; Wiley-VCH Verlag Gmbh & Co. KGa.

George Devitt et al; "Mechanisms of SARS-CoV-2 Inactivation using UVC Laser Radiation" bioRxiv preprint Feb. 3, 2023.; https://doi.org/10.1101/2023.02.03.526944doi.

Ernest R. Blatchley, III et al; "SARS-CoV-2 Ultraviolet Radiation Dose-Response Behavior"; Journal of Research of the National Institute of Standards and Technology; vol. 126, Article No. 126018 (2021) https://doi.org/10.6028/jres.126.018.

Ernest R. Blatchley, III et al; "Far UV-C Radiation: Current State-of Knowledge" International Ultraviolet Association; Whitepaper of The IUVA Task Force (TF) on Far UV-C Radiation for Disinfection of Air and Surfaces; May 14, 2021. https://iuva.org/Projects-Articles-Repository/10503221.

Minna M. Hankaniemi et al "A comparative study of the effect of UV and formalin inactivation on the stability and immunogenicity of a Coxsackievirus B1 vaccine" Vaccine 37 (2019) 5962-5971; Elsevier; Mar. 22, 2019; https://doi.org/10.1016/j.vaccine.2019.08.03.

Joshua Hadi et al; "Control Measures for SARS-CoV-2: A Review on Light-Based Inactivation of Single-Stranded RNA Viruses" Pathogens 2020, 9, 737; doi:10.3390/pathogens9090737; http://www.mdpi.com/journal/pathogens.

Chieh-Wen Lo et al. "UVC Disinfects SARS-Co-V2 By Induction of Viral Genome Damage Without Apparent Effects on Viral Morphology and Proteins" Nature Portfolio Scientific Reports | (2021) www.nature.com/scientificreports.

Loveday, E.K.; Hain, K.S.; Kochetkova, I.; Hedges, J.F.; Robison, A.; Snyder, D.T.; Brumfield, S.K.; Young, M.J.; Jutila, M.A.; Chang, C.B.; et al. Effect of Inactivation Methods on SARS-CoV-2 Virion Protein and Structure. Viruses 2021, 13, 562. https://doi.org/10.3390/v13040562.

Naomi Takasuka et al; "A subcutaneously injected UV-inactivated SARS coronavirus vaccine elicits systemic humoral immunity in mice" International Immunology, vol. 16, No. 10, pp. 1423-1430; 2004; The Japanese Society for Immunology; doi:10.1093/intimm/dxh143.

Ong, Q. et al; "Irradiation of UVC LED 277 nm inactives coronaviruses in association to photodegradation of spike protein;" Helion 8 (2022) e11132; www.cell.com/heliyon.

Renata Sesti-Costa et al; "UV 254 nm is more efficient than UV 222 nm in inactivating SARS-CoV-2 present in human saliva;" Photodiagnosis and Photodynamic Therapy 39 (2022) 103015; https://doi.org/10.1016/j.pdpdt.2022.103015.

Sanjeev K. Bhardwaj et al "UVC-based photoinactivation as an efficient tool to control the transmission of coronaviruses" Science of the Total Environment 792 (2021) 148548; www.elsevier.com/locate/scitotenv.

Beck, Sara E. et al. "Wave-length dependent Damage to Adenoviral Proteins Across the Germacidal UV Spectrum" Environ. Sci. Technol. 2018, 52, 223-229.

Koma T, Doi N, Suzuki A, Nagamatsu K, Yasui T, Yasutomo K, Adachi A, Minamikawa T and Nomaguchi M (2022) Major target for UV-induced complete loss of HIV-1 infectivity: A model study of single stranded RNA enveloped viruses. Front. Virol. 2:994842. doi: 10.3389/fviro.2022.994842.

W. C. Russell; "Adenoviruses: update on structure and function;" Journal of General Virology (2009), 90, 1-20; DOI 10.1099/vir.0.003087-0.

\* cited by examiner

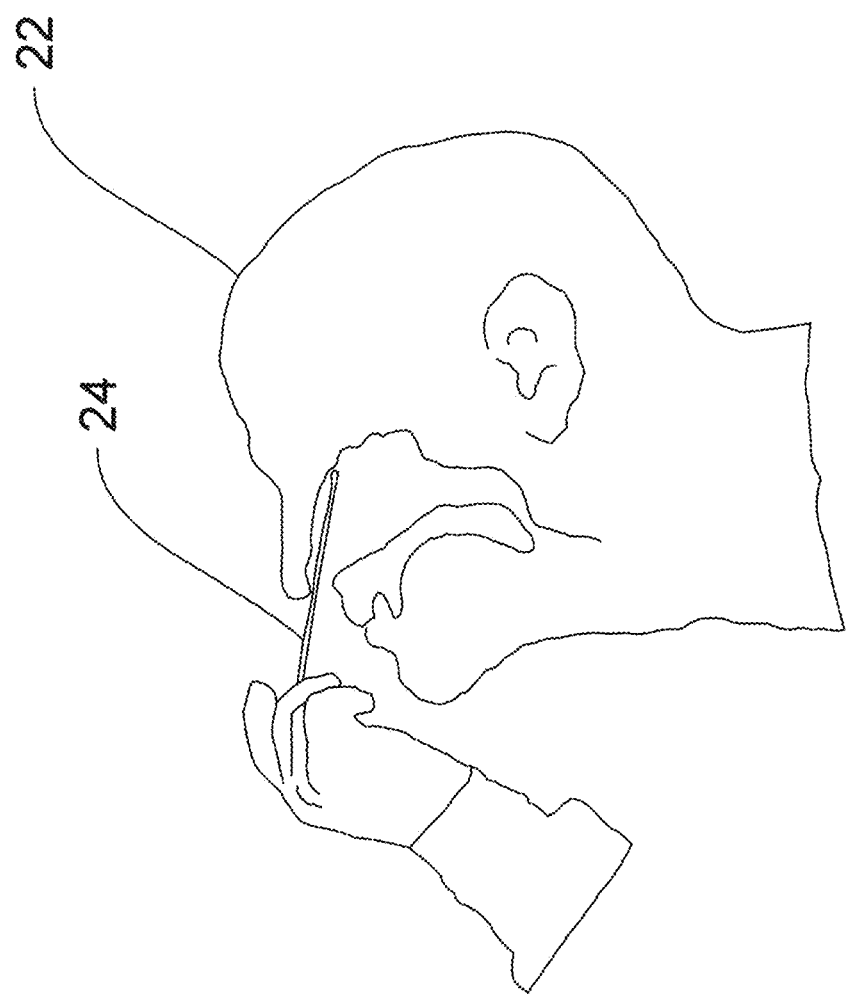
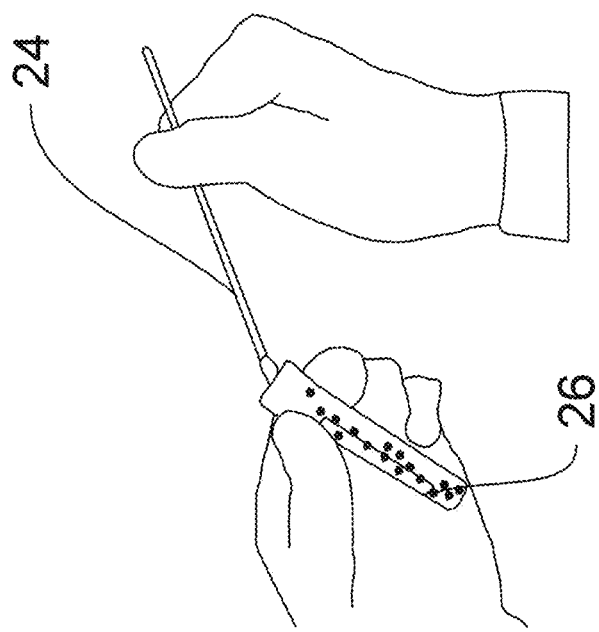
FIG.2A
FIG.2B

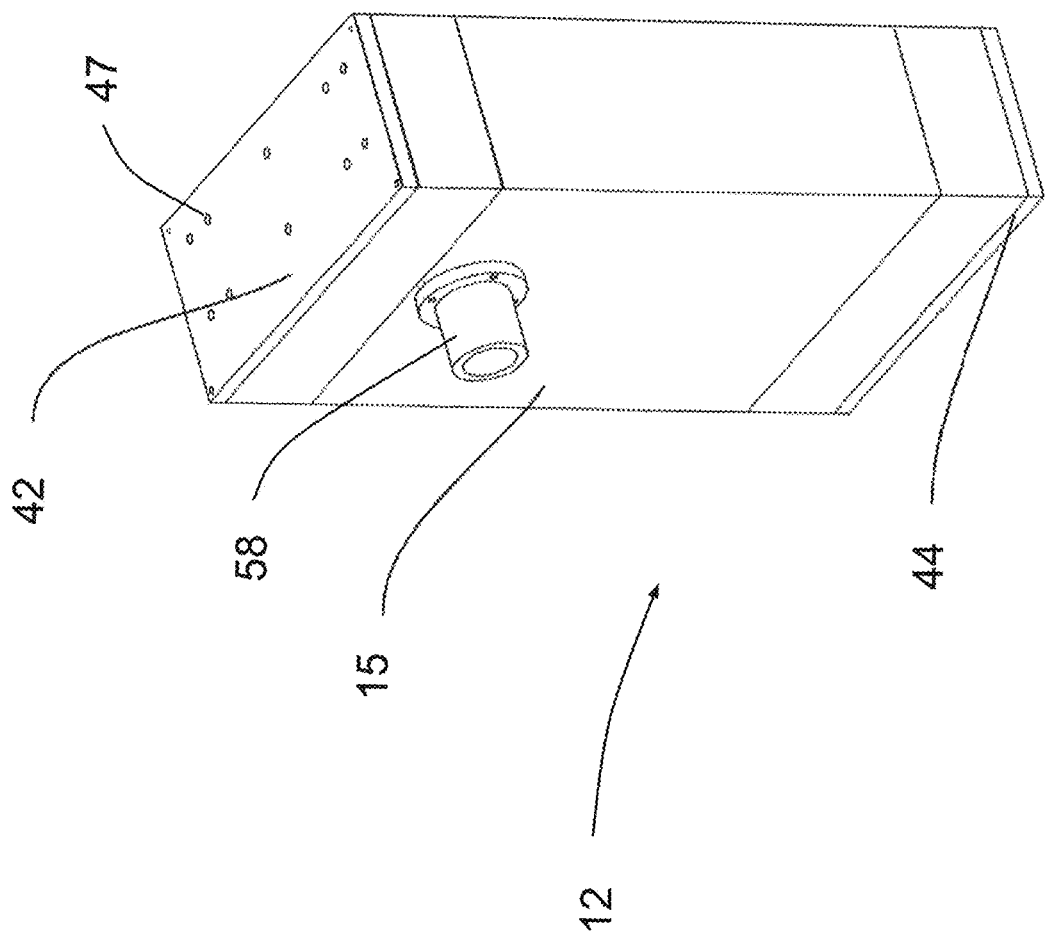

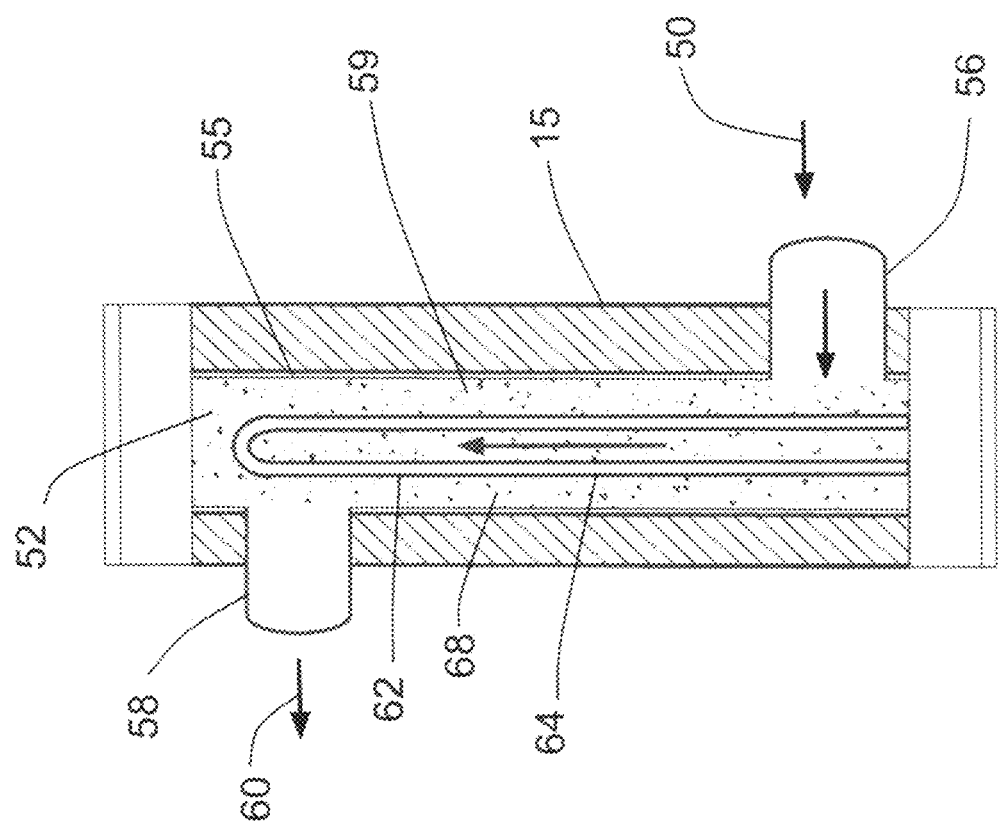
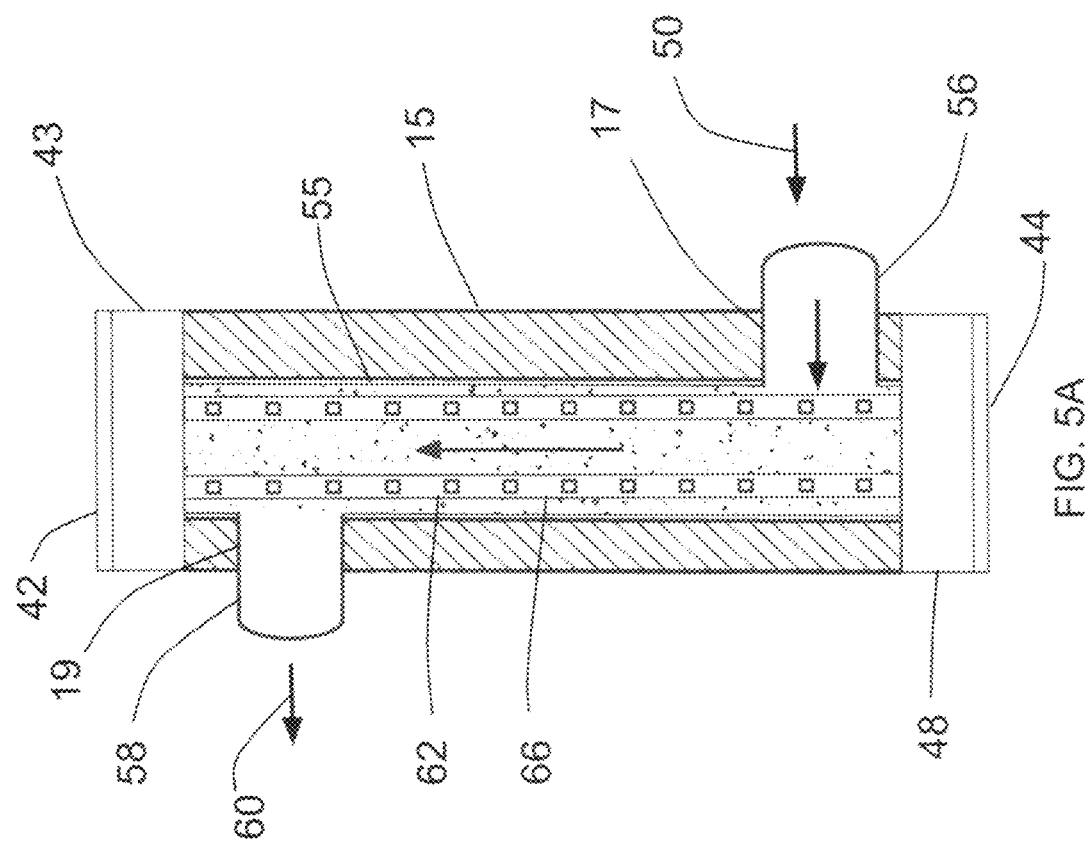

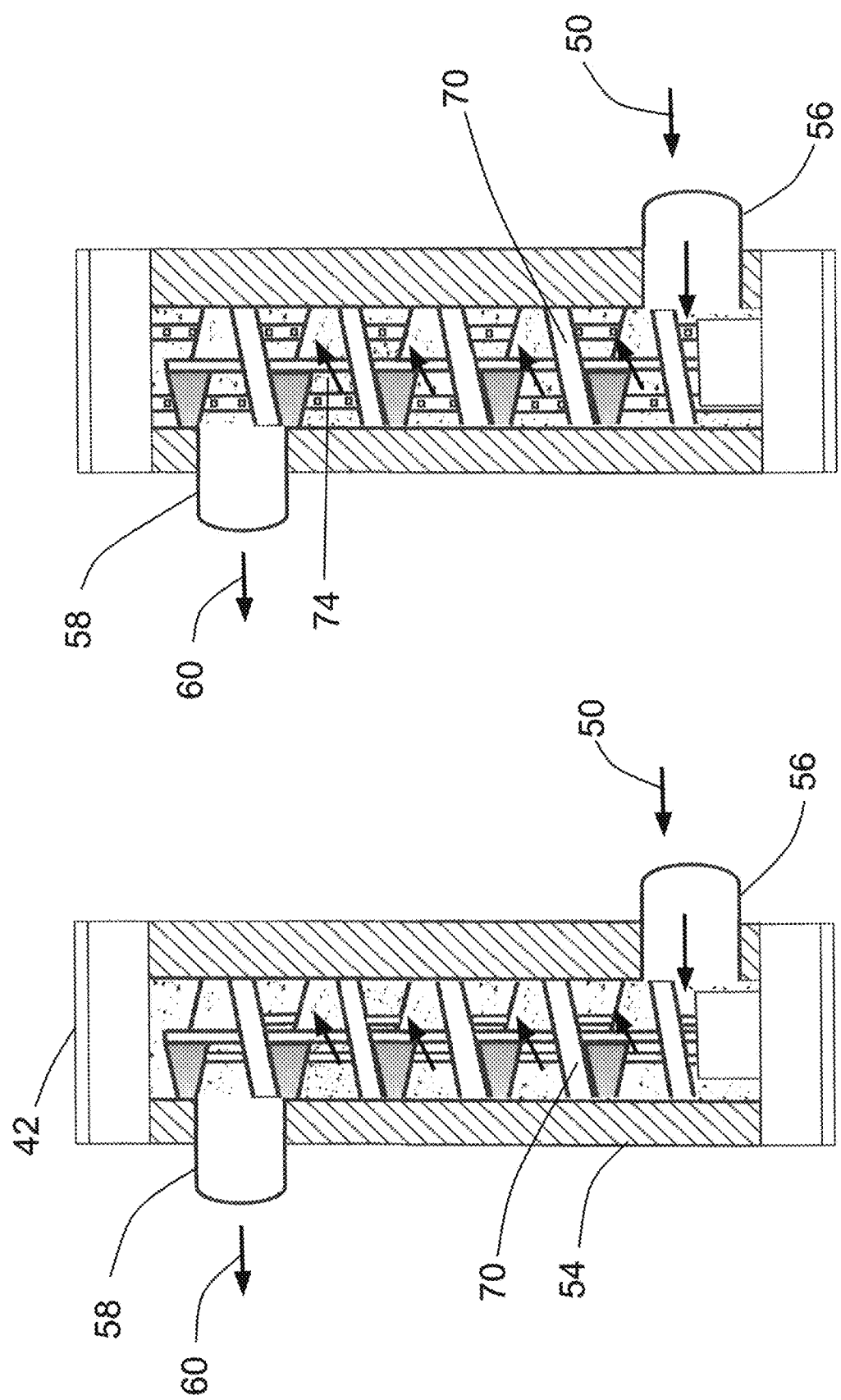

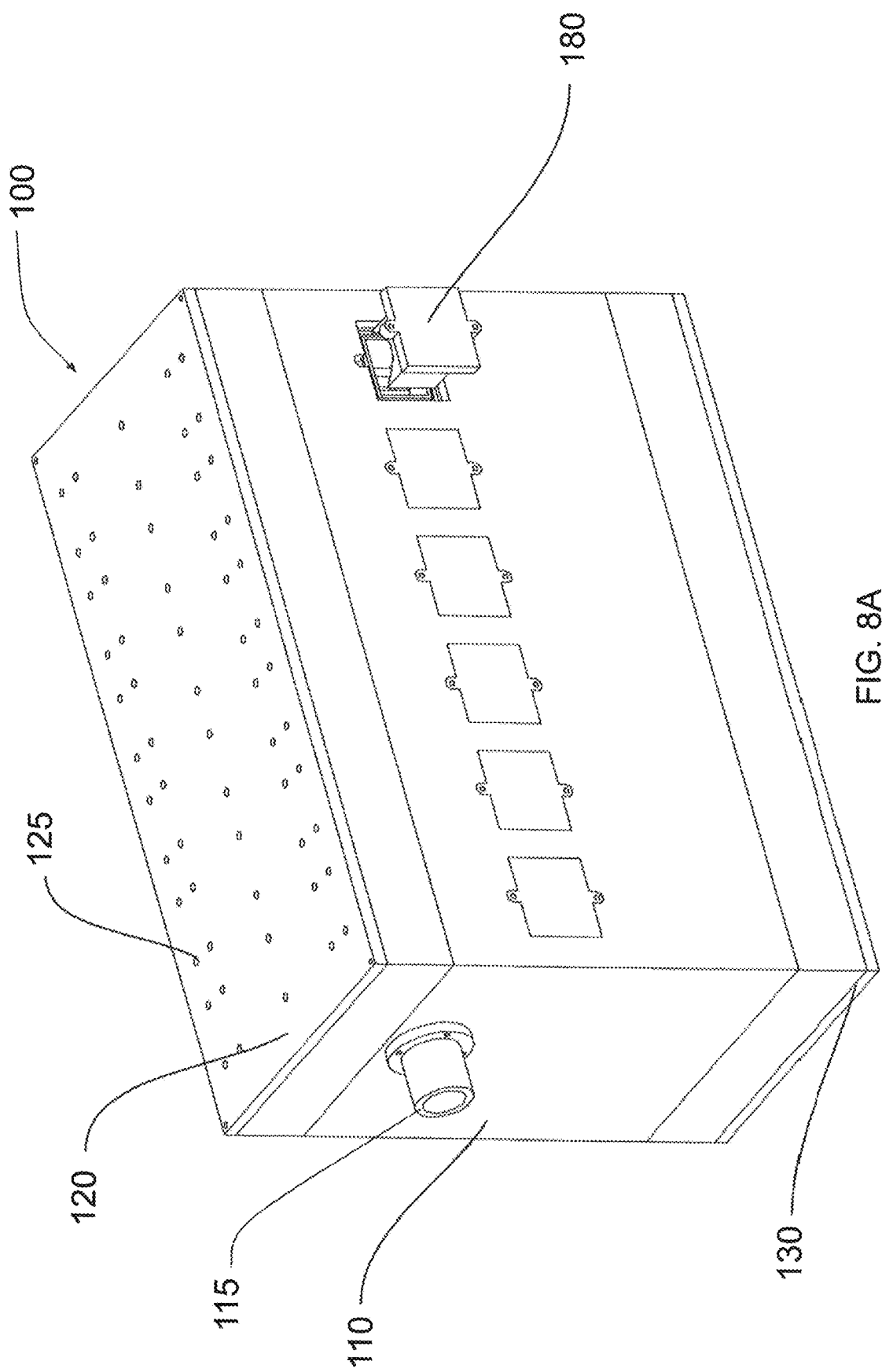

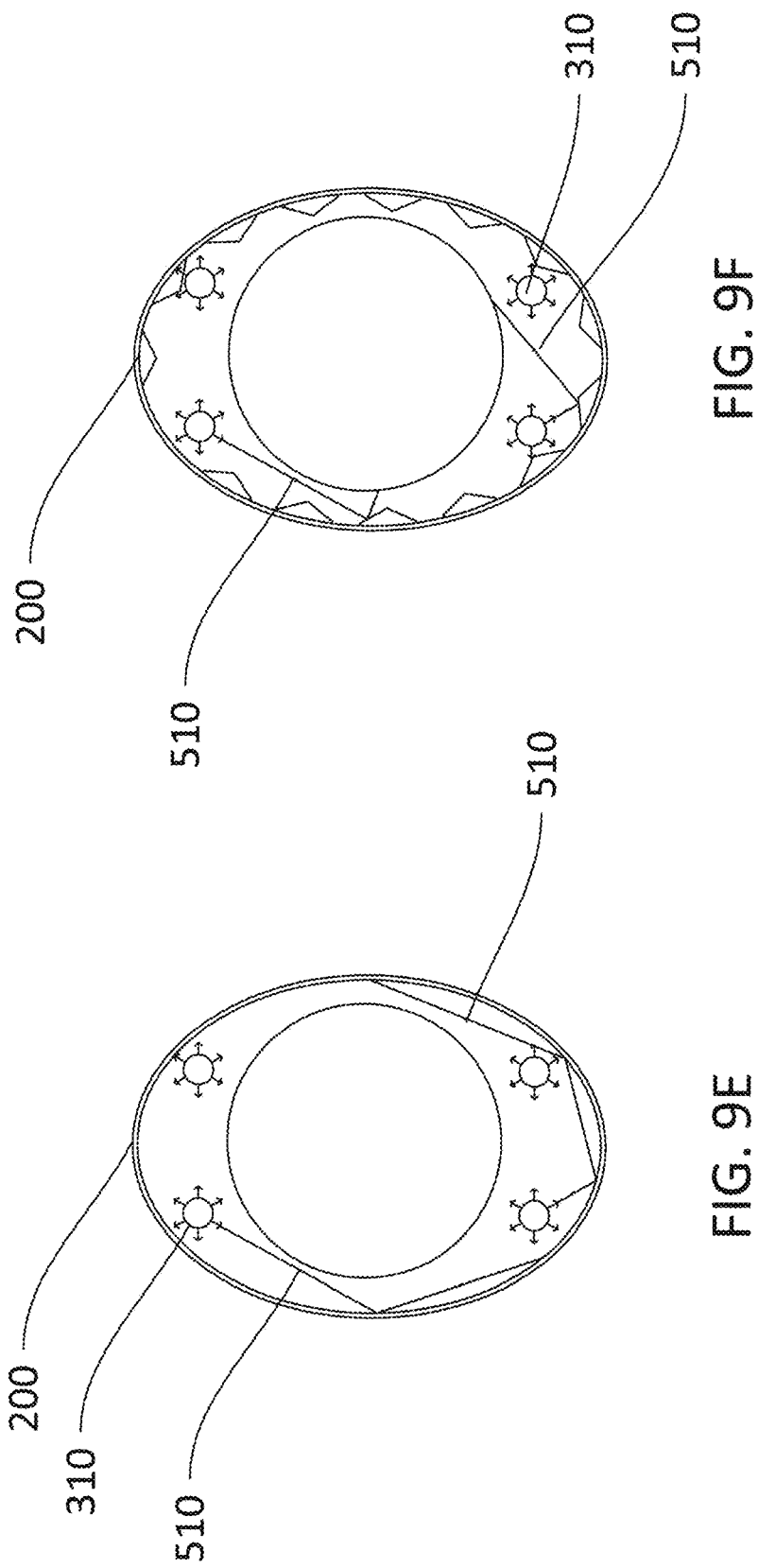

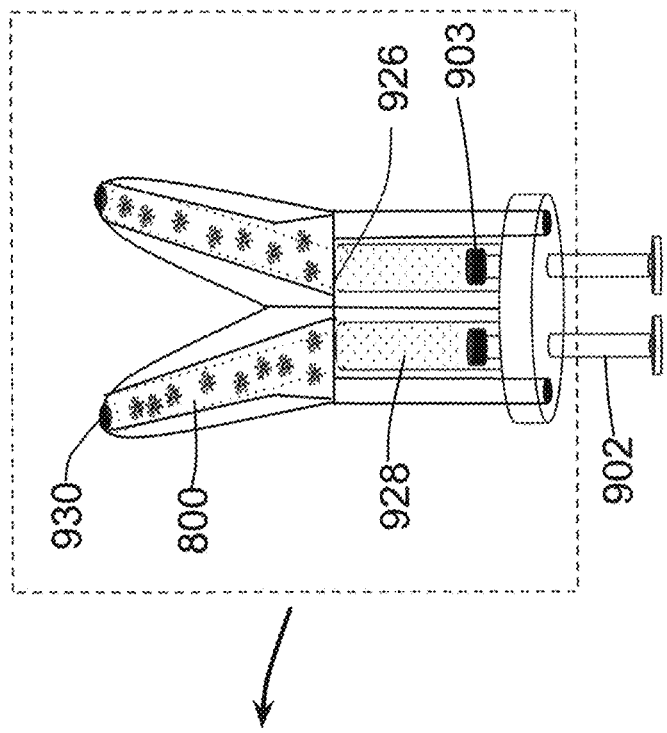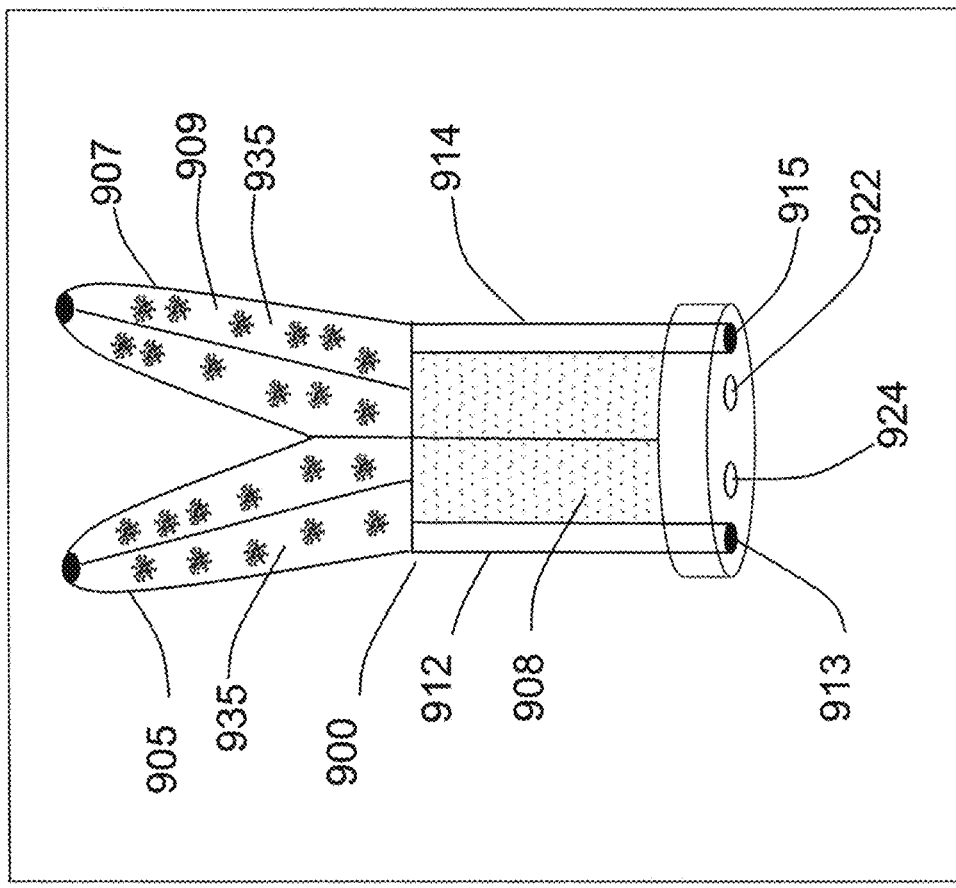
FIG. 13A
FIG. 13B

SYSTEMS AND METHODS FOR THE PREPARATION OF VACCINES UTILIZING PREDICTABLY INACTIVATED PATHOGENS

CROSS REFERENCE TO RELATED APPLICATIONS

This application claims priority to and is a continuation in part of U.S. Ser. No. 17/545,822 filed on Dec. 8, 2021, which is a non-provisional application of and claims priority to U.S. Ser. No. 63/233,697 filed on Aug. 16, 2021. This application is also a non-provisional application of and claims priority to U.S. Provisional Patent Application Ser. No. 63/353,369 filed on Jun. 17, 2022, U.S. Provisional Patent Application Ser. No. 63/359,381 filed on Jul. 8, 2022, and U.S. Provisional Patent Application Ser. No. 63/401,817 filed on Aug. 29, 2022, the entire disclosures of which are part of the disclosure of the present application and are hereby incorporated by reference in their entireties.

FIELD OF THE INVENTION

The present invention relates to a method for producing a vaccine from a neutered pathogenic source. The neutered pathogenic source may be a SARS-COV-2 virus that is neutered with a defined dose of UV-C light. The neutered SARS-COV-2 viral vaccine is administered through an inhalation pump, orally, or parenterally. The architecture of the neutered inactivated virus can be kept intact or partially destroyed by using graded dosage of the UVC.

BACKGROUND

The background description includes information that may be useful in understanding the present invention. It is not an admission that any of the information provided herein is prior art or relevant to the presently claimed invention, or that any publication specifically or implicitly referenced is prior art In the struggle for the humans to fight and survive against the viruses and bacteria which are the original occupants and landlords of our planet, vaccines have played a major role. From the time whole live virus (cowpox in 1796) was used as the vaccine in a quasi-scientific adventure to the present day dealing with extensively thought out and investigated use of SRS-COV-2, S protein subunit vaccines, our struggle to survive and claim our occupancy in this planet has seen many ups and downs. In the process, we have used tamed (attenuated) live viruses, killed (and mutilated) whole virus vaccines, and various forms of subunit vaccines through recombinant (forced marriage) methods. Most of the presently available COVID-19 vaccines belong to this third group. Undoubtedly all three varieties of vaccines have advantages and disadvantages to consider.

Social distancing and the use of personal protective equipment (PPE), such as mask and face shields, have been recommended to protect individuals and control the spread of airborne viruses, such as, SARS-CoV-2 (or the COVID-19) virus. However, these measures may not be sufficient to contain the spread of the COVID-19 virus especially in confined spaces. Most face masks have questionable ability to block fine virus particles. In infected individuals, the masks block the escape of large virus droplets thus forcing them to breath in more and more viruses with each breath and reinfect themselves with the viruses they should be expelling. Social distancing is of questionable value in a facility where people move around because the virus droplets take eight minutes or more to drop from a height of five feet. Inevitably, a virus "halo" from the infected person lies in wait for the next person to pass by. Lockdowns have only temporary value because the virus is still present in the ambient air when the lockdown is lifted.

To be effective, the virus has to be destroyed or neutered and the battle should be preferably outside the body since we do not yet know the long-term complications suffered by individuals who are supposedly "cured" of neither the COVID-19 virus nor the long-term effects of current vaccines. Recent studies have found that the COVID-19 virus and other variants spread not only through close personal contacts but also through long distance and for extended periods through the air. Even if the virus droplets fall down within a six-foot radius, the viruses in these droplets are not destroyed. Instead, these droplets dry up, release the virus particles of about 0.1 micron to float into the air converting rooms, buildings, airplanes, etc. into something similar to smoke filled facilities. Even an N95 mask cannot block these particles completely.

For example, the COVID-19 virus can infect buildings, airplanes, buses, trains and other structures that have inadequate disinfection functionality in the associated air conditioning system or in air conditioners with sluggish air movement. Such air conditioners can function as a "vector equivalent" for the COVID-19 virus and other microorganisms. Individuals in confined/enclosed spaces are constantly exposed to this deadly virus every time they inhale the air from such an infected building, structure or conventional mask. Neither the air conditioning system nor a conventional mask may be able to protect these individuals because either the masks cannot block such fine virus particles or the masks that can partially block such particles eventually fail due to overloading. Ideally, the air conditioner system can be upgraded to protect against the COVID-19 virus and other microorganisms.

The only long term solution is to develop a multivalent vaccine that can prevent the infection of individuals with the COVID-19 virus. If there are few adults that become infected with the virus, the virus is unlikely to have a chance to mutate into a strain that can bypass the antibodies created in response to a multivalent vaccine, Therefore, there is an ongoing need to provide better COVID-19 vaccines designed to protect society and individuals from the COVID-19 virus.

SUMMARY

One embodiment of the present invention includes a process for developing neutered whole pathogen vaccines involving the destruction of the RNA or DNA of the pathogen by using germicidal UV-C radiation. One embodiment of the present invention is a process for developing neutered whole viral vaccines that utilize the destruction of the RNA or DNA of the virus using germicidal UVC (or UV-C) radiation. For instance, the SARS-COV-2 virus can be neutered by destruction of its RNA using UV-C in a dose related manner.

Another embodiment of the present invention includes a process of neutering a pathogen in a disinfection unit comprising a housing that is opaque to UVC enclosing a chamber that has (a) a chamber wall that is transparent to UV-C light, (b) a chamber inlet, (c) a chamber outlet, (d) a centralized inner bore, (e) an interior chamber surface facing the inner bore; (f) a UV-C light source positioned adjacent the interior surface; and (g) a helical air flow diverter centralized within the inner bore proximate to the UV-C light source, wherein the helical airflow diverter creates a helical path for the airflow pathway as the airflow pathway proceeds from the chamber inlet to the chamber outlet, resulting in a centrifugal force, pushing contaminants to the periphery close to the UV-C light source.

Another embodiment of the present invention includes administering the vaccine derived from a neutered whole virus through a nasal inhalation process. An inhalable vaccine simplifies the application process and can greatly improve the acceptance of the vaccine by the general population. SARS-COV-2 infects the cells by binding its spike on the ACE2 proteins on the cell surface. A neutered virus with its intact spikes will bind to the same ACE2 proteins thereby blocking the virus' entry into the cell.

Another embodiment of the present invention includes an inhalation pump comprising: (a) a first half and a second half, wherein each half has a top compartment and an adjoining bottom compartment; (b) a fill line associated with each half, the fill line having a septum on a bottom end and a top end that enters a central bore in the top compartment; (c) each bottom compartment is filled with compressed air and has a moveable end at its bottom end; and (d) each top compartment has a releasable cap at its top end.

According to yet another embodiment, a method of administering a neutered pathogenic inoculum into a nasal cavity of a patient comprising: (a) preparing a neutered pathogenic inoculum; (b) loading the neutered pathogenic inoculum into a central bore of a top compartment of an inhalation pump, wherein the top compartment has a top end that is capped with a removable cap and a moveable bottom end that adjoins a bottom compartment; (c) filling the bottom compartment with a compressed air; (d) attaching a syringe to a moveable lower end of the bottom compartment; (e) removing the cap from the top end of the top compartment; and (f) pushing a syringe plunger upward to force the inoculum into a patient's nostril.

According to yet another embodiment, a method of quantitating damage to a pathogenic source comprising: (a) preparing a standardized pathogenic source; (b) treating the pathogenic source with a known dosage of UV-C radiation; (c) collecting the UV-C treated pathogenic source; (d) assessing an amount of damage to a genetic material of the UV-C treated pathogenic source; and (e) assessing an amount of damage to one or more proteins of the UV-C treated pathogenic source.

Various objects, features, aspects and advantages of the inventive subject matter will become more apparent from the following detailed description of preferred embodiments, along with the accompanying drawing figures in which like numerals represent like components

BRIEF DESCRIPTION OF THE DRAWINGS

The invention will be described in further detail below and with reference to the attached drawings, which describe or relate to methods and devices of the present invention.

FIG. 2A illustrates an active virus harvested from an active patient with a nasal swab.

FIG. 2B illustrates the nasal swab from FIG. 2A being used to infect a cell culture.

FIG. 4 is a perspective view of one embodiment of a UV-C air disinfection unit.

FIGS. 5A-5C illustrate a sectional side view of embodiments of the air disinfection unit shown in FIG. 4.

FIGS. 6A and 6B illustrates the air flow path around a helical air flow diverter in the sectional side view of the air disinfection unit.

FIG. 8A is a perspective view of one embodiment of a UV-C air disinfection unit.

FIGS. 9E-9H illustrate light reflections in an inner bore coated with and without an irregular or crenulated surface.

FIGS. 13A-13B illustrate one embodiment of a nasal inhalation pump.

DETAILED DESCRIPTION

Figure 1:
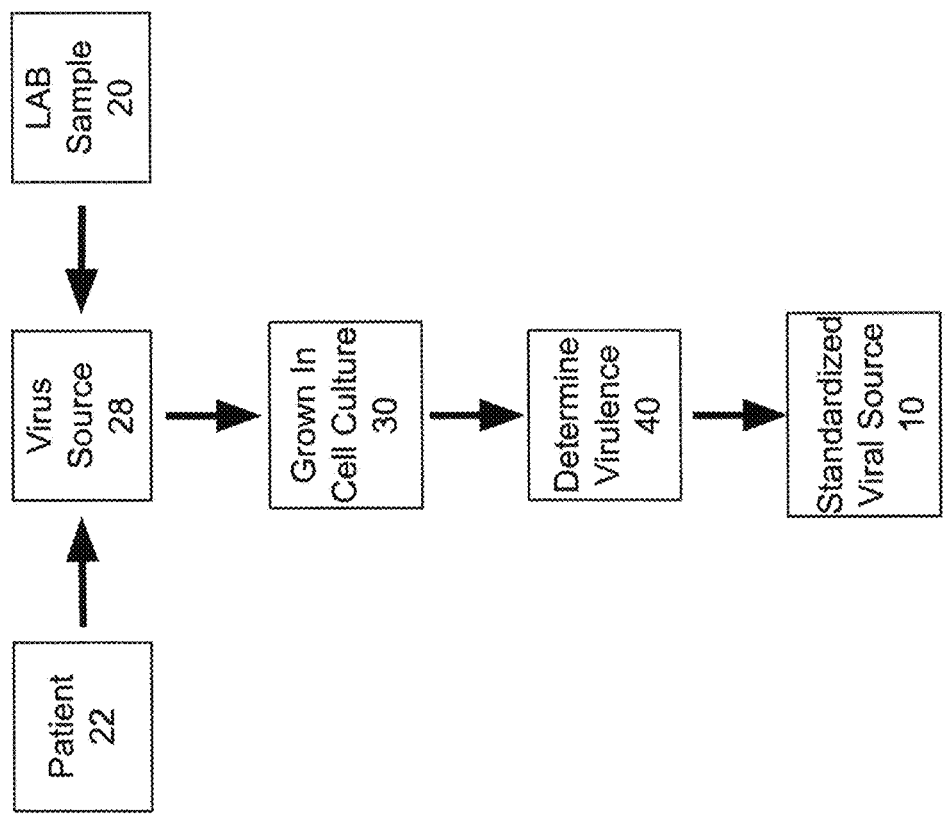
FIG. 1 is a schematic representation of the preparation of a standardized virulent viral source.

The present invention relates to a method for producing a vaccine from a neutered pathogenic source. The neutered pathogenic source may be a SARS-COV-2 virus that is neutered with a defined dose of UV-C light. The neutered SARS-COV-2 viral vaccine may be administered though an inhalation pump, orally, or parenterally.

Characteristics and advantages of the present disclosure and additional features and benefits will be readily apparent to those skilled in the art upon consideration of the following detailed description of exemplary embodiments. It should be understood that the description herein, being of example embodiments, is not intended to limit the claims of this patent (or any patent claiming priority hereto). On the contrary, the intention is to cover all modifications, equivalents and alternatives falling within the spirit and scope of this disclosure and the appended claims. Many changes may be made to the particular embodiments and details disclosed herein without departing from such spirit and scope. For instance, although SARS-COV-2 is often used as an example of the invention, it is understood that the methods and devices disclosed herein can be used for other viruses and pathogens.

As used herein and throughout various portions (and headings) of this patent (including the claims), the terms "invention", "present invention" and variations thereof are not intended to mean every possible embodiment encompassed by this disclosure or any particular claim(s). Thus, the subject matter of each such reference should not be considered as necessary for, or part of, every embodiment hereof, or of any particular claim(s), merely because of such reference. Each of the appended claims defines a separate invention, which for infringement purposes is recognized as including equivalents to the various elements or limitations specified in the claims. Depending on the context, all references below to the "invention" may in some cases refer to certain specific embodiments only. In other cases, it will be recognized that references to the "invention" will refer to subject matter recited in one or more, but not necessarily all, of the claims. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (for instance, "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined, it should be given the broadest definition persons in the pertinent art have given that term as reflected in printed publications and issued patents at the time of filing.

One embodiment of the present invention includes a method for producing a vaccine from a neutered pathogenic source. The neutered pathogenic source may be a SARS-COV-2 virus that is neutered with a defined dose of UV-C light. Some embodiments of the invention administer the neutered SARS-COV-2 virus through an inhalation pump, orally, or parenterally.

One embodiment of the present invention includes a process for producing a vaccine to a predictably inactivated pathogen, such as a virus. The process comprises standardizing a virulent pathogenic source; titrating the degree of ultraviolet inactivation of the pathogenic source; and preparing an inoculum, or vaccine, to produce or increase immunity to the inactivated pathogenic source.

The embodiments described below include processes for producing a vaccine to a standardized inactivated viral source, but such embodiments may be used to produce vaccines to other pathogens, such as bacteria or other microbes.

Another embodiment of the present invention includes an inhalation pump and processes for filing the pump and using it to deliver a vaccine into a person's nasal cavities.

Standardizing a Virulent Pathogenic Source

First, one must obtain a virulent pathogenic source having a known pathogen quantity and activity per microliter (μl). One method of how this can be achieved is illustrated in FIG. 1 using a virus as the pathogenic example.

Figure 3B:
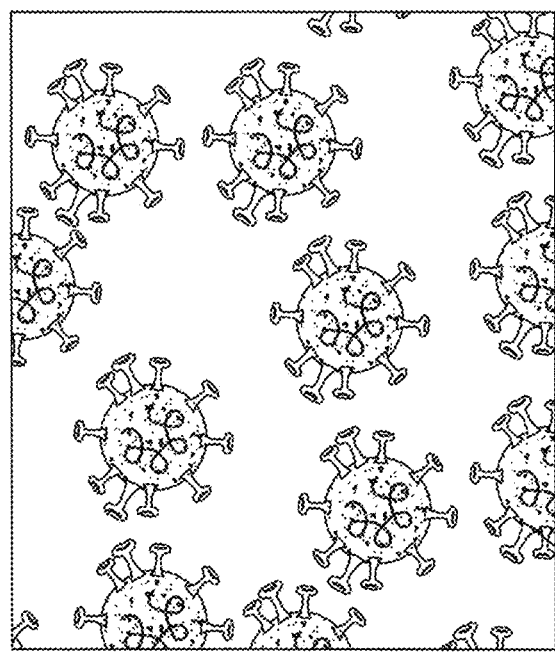
FIG. 3B is a schematic representation of SARS-COV-2 virus particles.
Figure 3A:
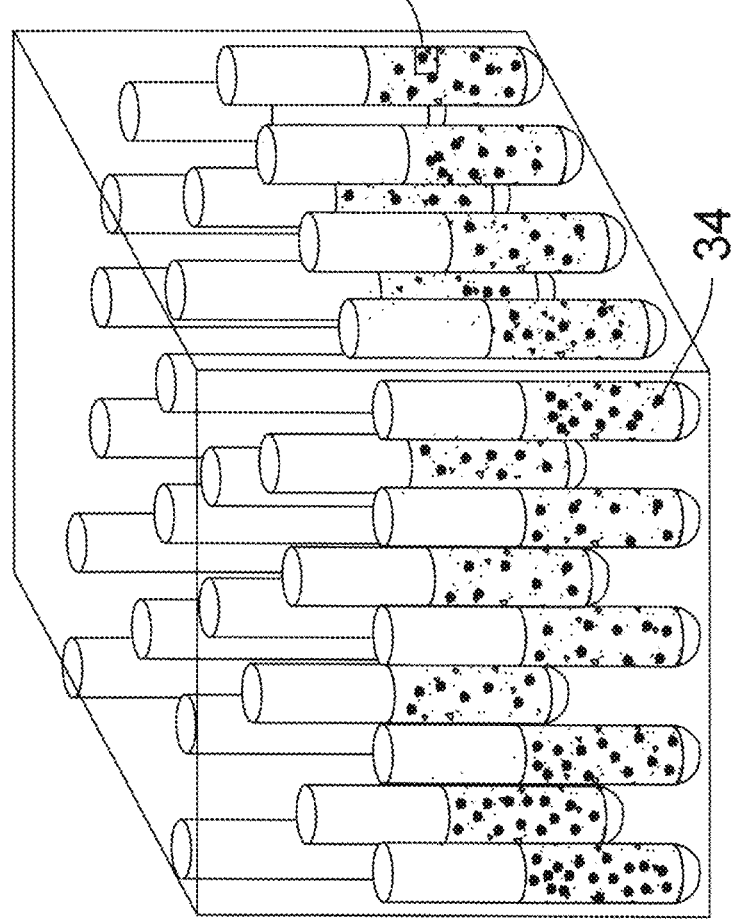
FIG. 3A illustrates the virus being grown in cell cultures.

A virus source 28, such as the SARS-COV-2 virus, is harvested from an active patient 22 as shown in FIGS. 2A and 2B or retrieved from a stored viral stock 20 from a laboratory. One embodiment of harvesting a viral source from a patient 22 is to use a cotton swab 24 to swab the nasal passage of the patient and then swirl the virus loaded swab in an appropriate cell culture media 26 to release the virus. The virus is typically replicated via the lytic cycle in host cells in cell culture 30. Once the virus enters the host cell, it makes new virus particles that are released into the extracellular fluid. Thus, numerous virus particles 34 are released into the cell culture media as indicated in FIG. 3A. A more detailed look at a SARS-COV-2 virus particle is shown in FIG. 3B. Viral virulence 40 or activity is generally tested by incubating the virus with cultured cells and observing the virus' cytopathic effects on the cells microscopically. The standardized viral source 10, or a viral suspension containing a known quantity of virus particles having a known activity per volume, is stored in aliquoted samples.

Ultraviolet Destruction of Pathogens

UV-C light is a well-known disinfectant. Many UV-C light emitting devices are available in the marketplace. These devices are used to "sterilize" surgical suites, airports, and other such spaces. However, for effective disinfection, the UV-C light has to be strong enough to destroy the microorganisms within a close proximity. Additionally, the microorganisms have to be exposed to the UV-C light for a sufficient duration of time before they are neutralized. Such high energy UV-C radiation and long exposure to UV-C radiation can injure normal human cells like skin, cornea, and other cells. Therefore, UV-C light should not be allowed to come near hands, face or other area of the skin. Furthermore, exposure of the skin to UV-C radiation can cause skin irritation and other ailments.

UV light is an electromagnetic radiation beyond the wavelength of the visible violet or beyond the spectrum that the human eye can see. The UV light itself has a spectrum ranging from a 100 nanometer to 400 nanometers. UV light having wavelengths from 315 nm to 400 nm is called UV-A, from 280 nm to 315 nm is called UV-B, and from 200 nm to 280 nm is called UV-C. Far UV-C light has a spectrum ranging from 207 nm-222 nm. For the purposes of this application, the terms "UV-C" and "far UV-C" are used interchangeably.

The earth's ozone layer blocks the UV-C, but allows UV-A and UV-B to reach earth. The shorter the light wavelength is, the less it will penetrate human skin. UV-A and UV-B can damage human skin and are the ones implicated in sunburn, skin cancer, and an increased risk of cataracts. UV-C from the sunlight cannot normally reach the earth because it is filtered out by the earth's ozone layer. Far UV-C and UV-C light penetration into the skin is low, but is sufficient to cause some damage. However, UV-C light penetrates microorganisms and denatures their RNA and/or their DNA, making the reproduction of those microorganisms impossible.

The kill rate of UV-C light depends on the specific microorganism you are trying to destroy as well as the UV-C dosage the organism receives. Dosage (J/m2) is a combination of exposure time and intensity (microwatts per square centimeter). UV_dose=UV_bulb_power*Exposure_time/(4*pi*UV_bulb_distance^2. The intensity is a measure of the power of the UV-C and its proximity to the organism, where Intensity, E=UV_bulb_power/UV_bulb_distance^2.

There are numerous ways to control the delivery of ultraviolet light to pathogens. One controllable delivery method is to employ one or more embodiments of the unique UV-C air disinfectant unit described below.

A UV-C Air Disinfection Unit

Disinfection Unit with Single Disinfection Chamber. One embodiment of a UV-C air purification disinfection unit 12, illustrated in FIGS. 4 and 5A-5B, has an opaque housing 15 with a housing inlet 17 and a housing outlet 19; a disinfectant chamber 52 with a transparent chamber wall 55, a chamber inlet 56, a chamber outlet 58, and a centralized inner bore 68 having an interior chamber surface 59 facing the inner bore; a UV-C light source 62 positioned adjacent the interior surface; and a helical air flow diverter 70 centralized within the inner bore proximal to the UV-C light source, wherein the helical airflow diverter creates a helical airflow path 74 for the air flowing from the chamber inlet to the chamber outlet.

Figure 5C:
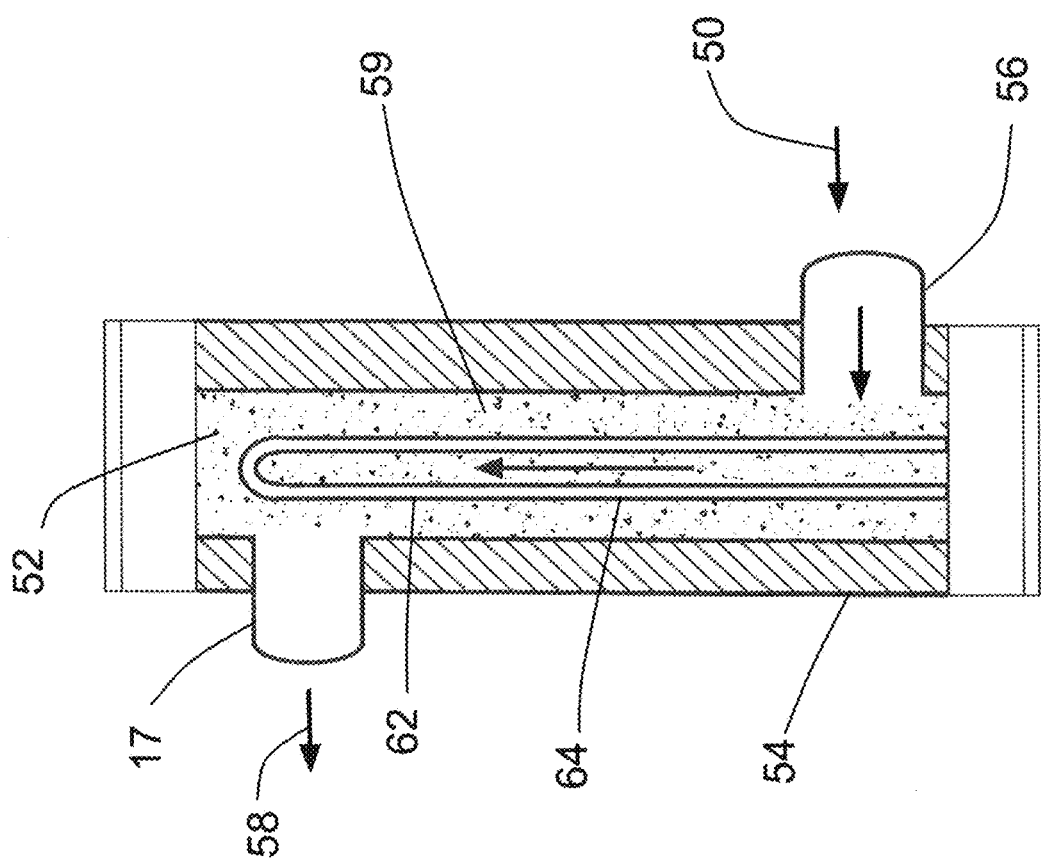

FIG. 5A illustrates isometric view of the embodiment with LEDs & inner UV transparent chamber wall but without showing helical air diverter. FIG. 5B is similar to FIG. 5A with UVC tubes instead of LEDs. FIG. 5C depicts an embodiment without inner UV transparent chamber without showing helical air diverter. FIG. 6A shows an embodiment with UVC tubes and helical air diverters without inner UVC transparent chamber wall. FIG. 6B is similar to FIG. 6A with LEDs instead of UVC tubes. A UV impenetrable housing 15 is important to protect the user of the unit and the environment around the unit from leaked UV light. The housing has a top lid 42 and a bottom lid 44. The top lid 42 has a number of holes 47 that allow the transfer of heat from one or more heat sinks to the outside air. The top lid also encloses the top ballasts 43. Similarly, the bottom lid 44 encloses the bottom ballasts 48 as also shown in FIG. 5A. The dimensions of the unit housing 15 can be varied to ensure the achievement of the desired disinfection of the airflow transversing the disinfection unit 12. The housing 15 may have an optional removable inspection window.

The air disinfection unit 12 has a single disinfection chamber 52. The disinfection chamber 52 is configured to house at least one UV light source 62 and a helical air flow diverter 70. The disinfection chamber 52 houses one UV-C light source 20 or a plurality of UV-C light sources. The disinfection chamber with its UV-C lights 62 and helical airflow diverter 70 irradiate the air flowing through the chamber from the chamber inlet 56 to the chamber outlet 58.

Disinfection Unit with Multiple Disinfection Chambers. Another embodiment of an air disinfection unit 100 has multiple disinfection chambers 200 as illustrated in FIGS. 8A-8D. The number of disinfection chambers may vary depending on the desired level of destruction of the pathogen as the pathogen-bearing air flows through the device.

Figure 8B:
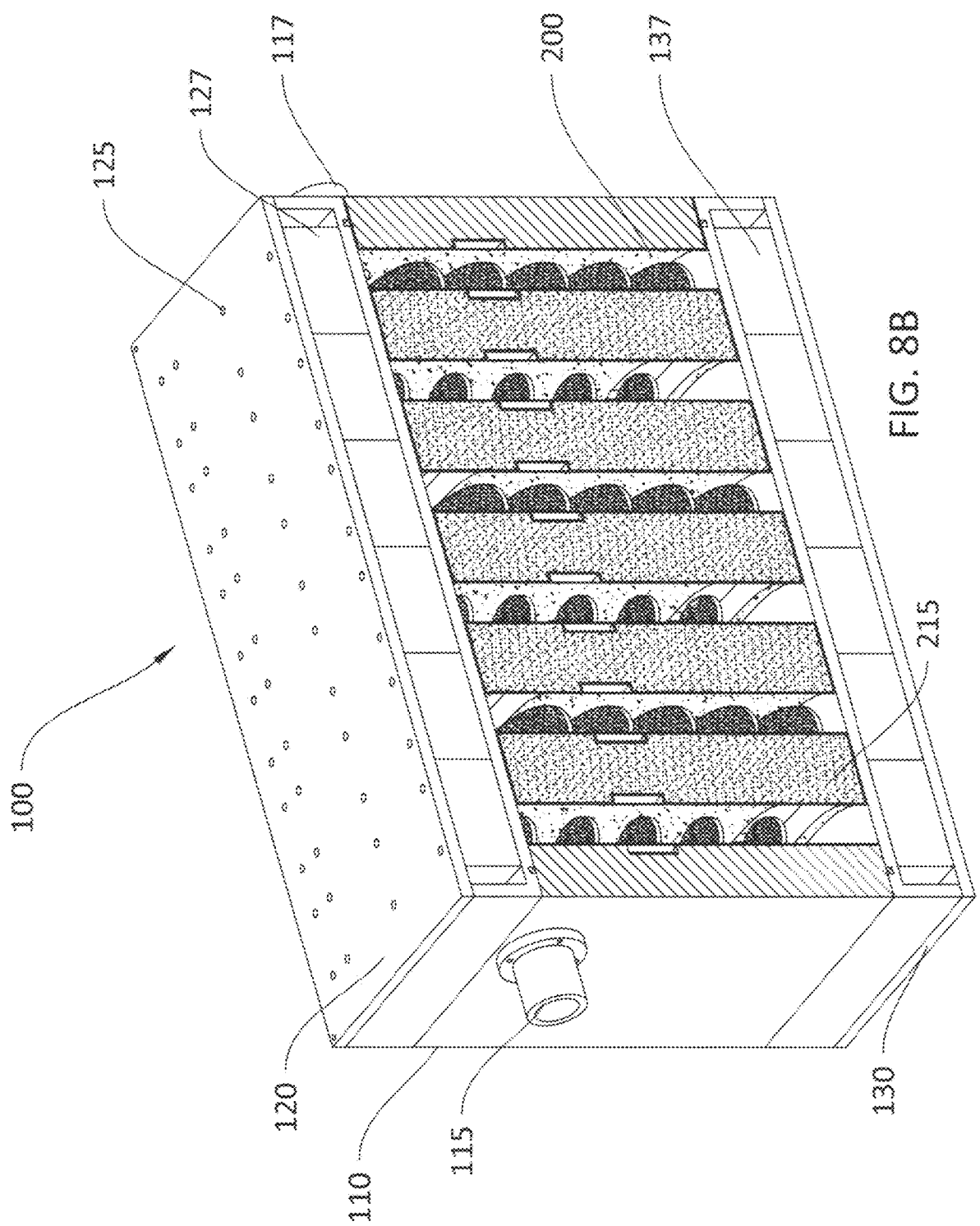
FIG. 8B is a perspective view of a side section of the air disinfection unit shown in FIG. 8A.

The air disinfection unit 100 has a similar housing to disinfection chamber unit 12. FIGS. 8A and 8B shows the housing 110 with a housing inlet 115 and a housing outlet 117. The housing 110 has a top lid 120 and a bottom lid 130. The top lid 120 has a number of holes 125 that allow the transfer of heat from one or more heat sinks to the outside air. The top lid also encloses the top ballasts 127. Similarly, the bottom lid 130 encloses the bottom ballasts 137. FIG. 8A shows an optional removable inspection window 180 for each disinfection chamber 200 of the device. The removable inspection window 180 in each disinfection chamber may be used to monitor the operation and viability of the components of the disinfection chamber as well as allowing an operator of the device to access the interior of the disinfection chamber as needed for maintenance of the internal components of the disinfection chamber 200.

Disinfection Chambers. The air purification units 12 and 100 have one or more disinfection chambers. Each chamber will have at least one UV-C light and a helical air flow diverter as described above. FIGS. 6A and 6B are isometric views of the interior of the air purification unit 12 and its disinfection chamber 52. The air inlet 56 allows the incoming air 50 to enter the disinfection chamber 52 at one end of the helical air flow diverter 70 and circulate around each rung of the helical air flow diverter 70 until the outgoing disinfected air 60 exits out the air outlet 58.

Figure 8C:
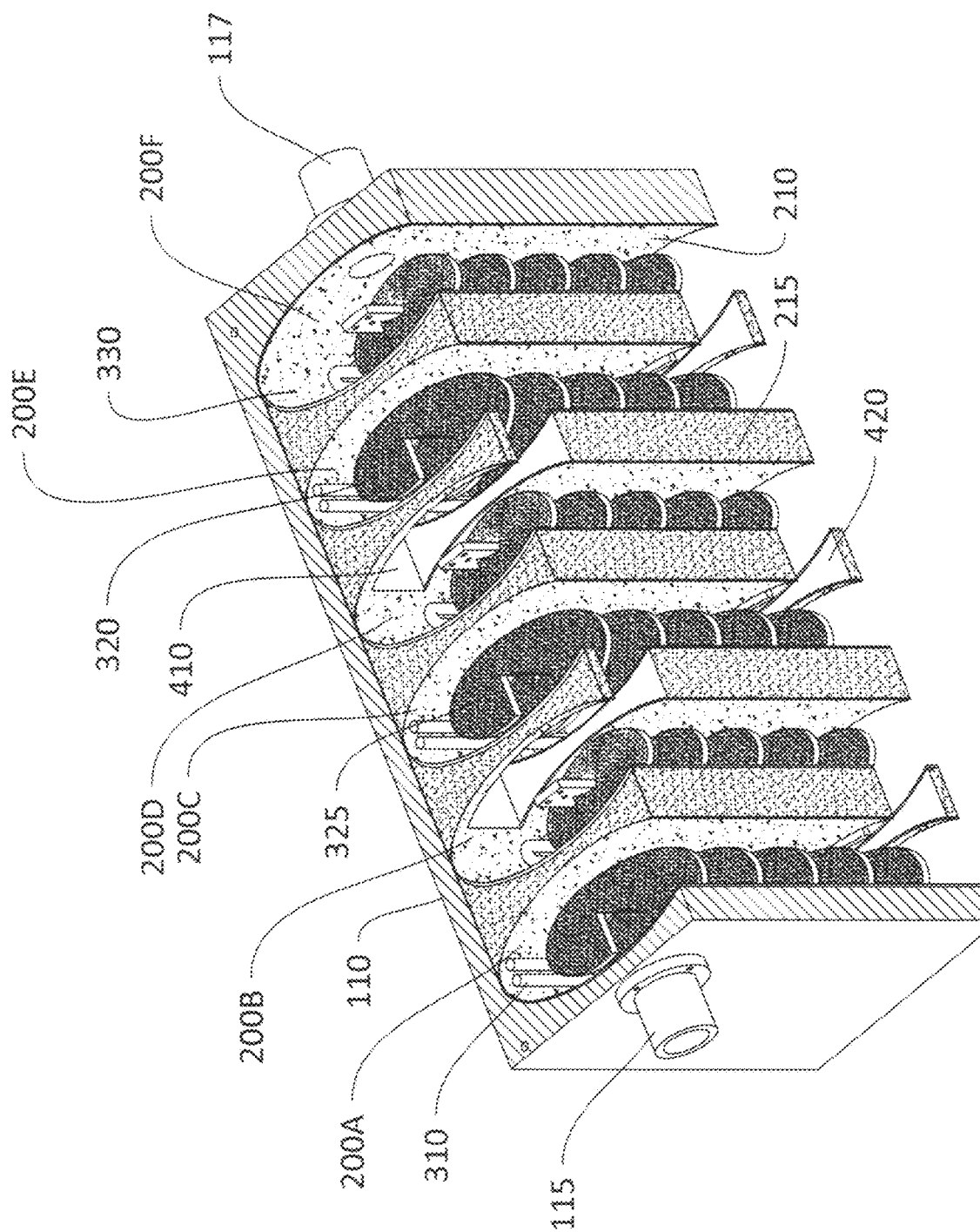
FIG. 8C is an isometric view of the air disinfection unit shown in FIG. 8B with its top lid and bottom lid removed.

FIG. 8B illustrates an isometric view of the interior of the air disinfection module 100. The module 100 has a number of disinfection chambers 200 between the inlet 115 and the outlet 117. The disinfection chambers 200 are separated by UV transparent chamber walls 215 and enclosed in a UV opaque housing 110. Each disinfection chamber 200 is configured to house at least one UV light source 310 and a helical air flow diverter 320 as shown in FIG. 8C. In one embodiment each disinfection chamber houses a plurality of UV-C light sources, such as the UV-C tubes shown in FIG. 8C. Each disinfection chamber with its UV-C lights 310 and helical airflow diverter 320 irradiates the air flowing through the chamber. The air disinfection unit 100 may be configured with various different dimensions as selected to fit the needs of the user, including variable heights and widths. For example, an increase in the width of the device allows for the inclusion of more disinfection chambers, whereas an increase in the height of each chamber allows for a longer air disinfection path through each disinfection chamber 200.

Figure 8D:
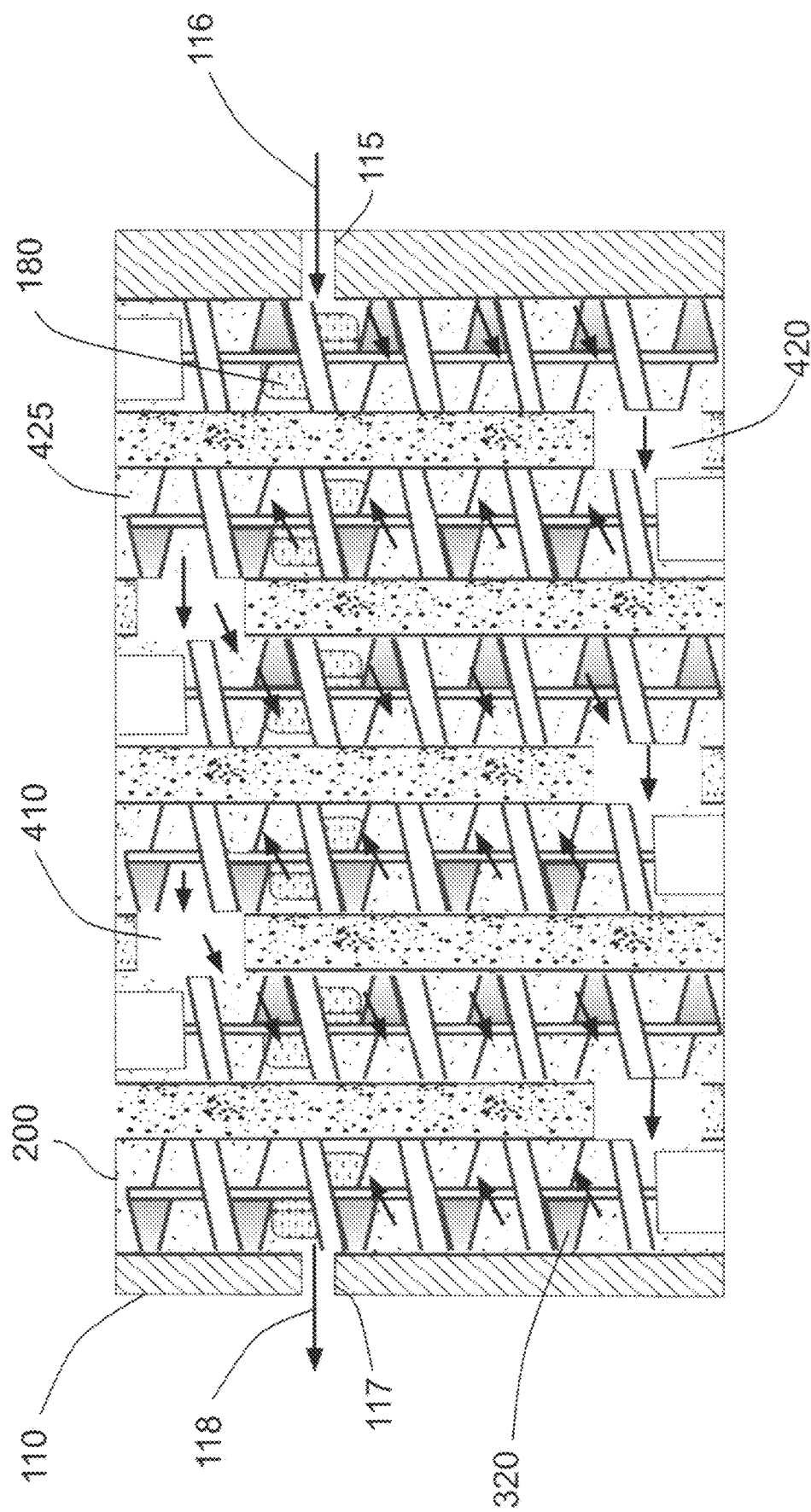
FIG. 8D illustrates a side view of the air flow path through the disinfection chambers of the air disinfection unit shown in FIG. 8C.

Each disinfection chamber 200 is in fluid communication with its adjacent disinfection chamber(s). As illustrated in FIG. 8D, the solid walls of adjacent disinfection chambers 200 are connected via alternating upper air passages 410 and lower air passages 420 to create a serpentine air flow path from one disinfection chamber to another disinfection chamber along the length of the device (shown in FIG. 8C as 200A to 200F). In addition, the helical air flow diverter 320 provides a helical air flow passage within each of the chambers 200. This serpentine air flow path between adjacent disinfection chambers and the helical air flow path within each disinfection chamber (see FIG. 8D) provides increased exposure of the pathogens in the airflow from the inlet 115 to the outlet 117 to UV-C or far UV-C light emitted by the ultraviolet light sources for an extended and optimal duration, with close contact.

Figure 9D:
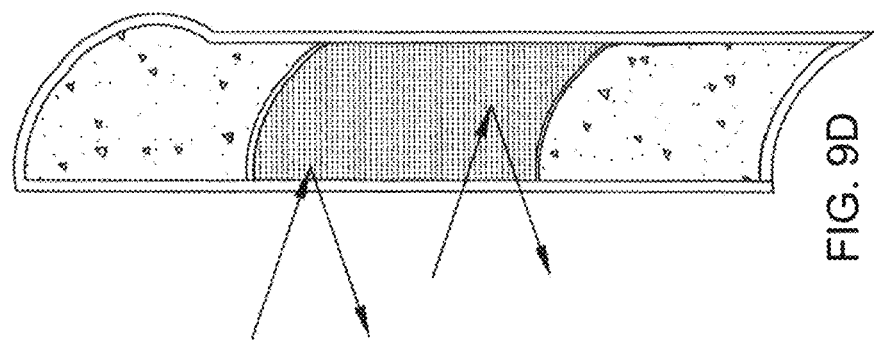
FIGS. 9A-9D illustrate different combinations of reflective surfaces and titanium dioxide layers.
Figure 9C:
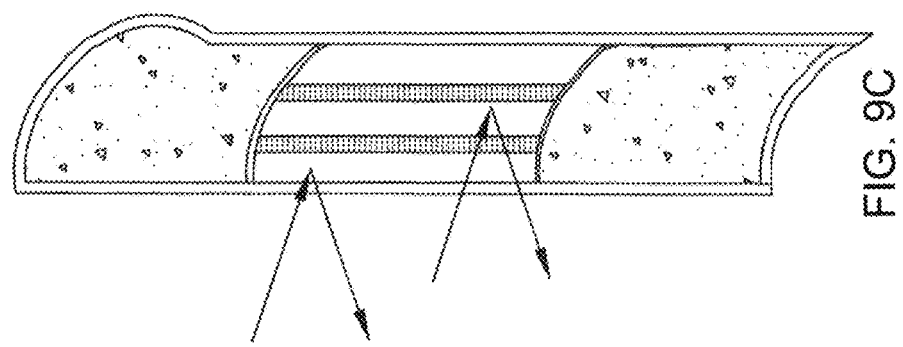
Figure 9B:
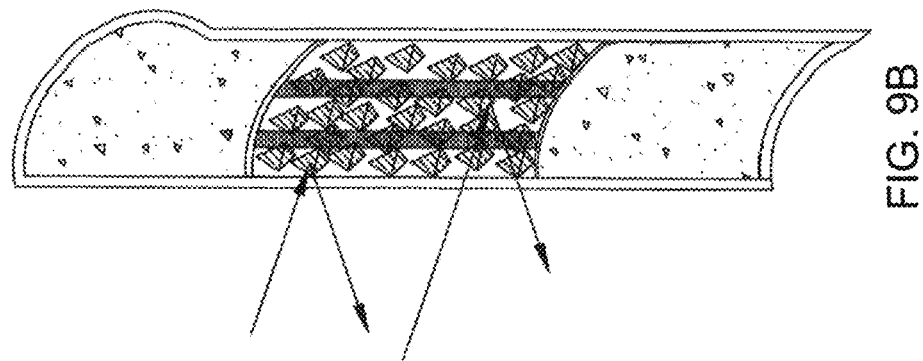
Figure 9A:
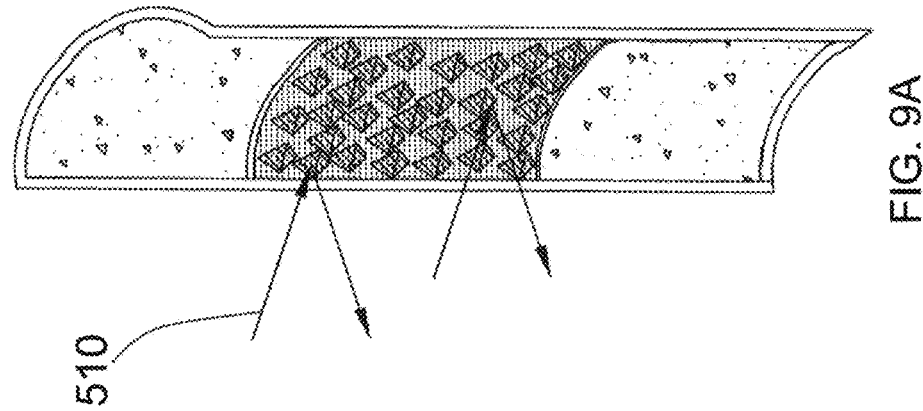
Figure 9H:
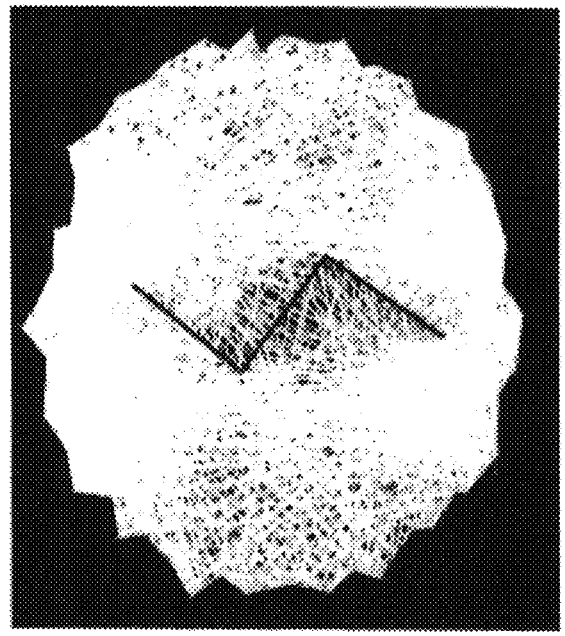
Figure 9G:
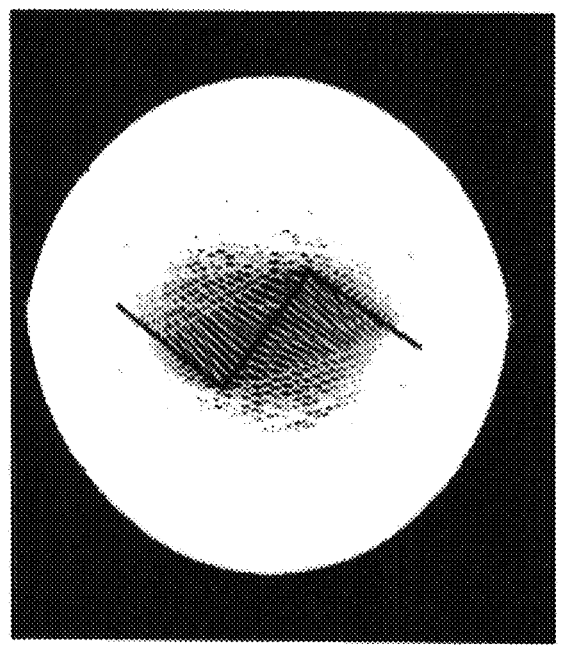

To further increase the effectiveness of the disinfection chamber 52 or 200, the internal chamber surfaces 59 or 210 respectively may be partially reflective and partially transparent optionally lined with transparent materials, reflective materials and/or titanium dioxide to concentrate the UV-C and also to make the device more lethal to the microorganisms in the air flow. As illustrated in FIGS. 9C and 9D, the reflective and titanium dioxide coatings can be coated one over the other or they can be in alternate up and down longitudinal strips inside the chambers.

In addition, as shown in FIGS. 9A-9B and FIGS. 9E-9H, the surface of these reflecting and titanium dioxide coated walls can be made irregular or crenulated to increase the light ray reflections. The multiple reflections 510 of the UV-C will impinge the pathogens on all sides, and the titanium dioxide can augment the lethality of the disinfection chamber towards all microorganisms. FIG. 8D shows the incorporation of reflecting and titanium dioxide coated walls 425 and irregular or crenulated areas (not shown) in the interior disinfection chamber wall 210 to increase the light ray reflections. Looking from the inside of the housing, the observation window 180 can be seen.

As previously discussed, the air flow path and therefore the time and exposure of the air flow to the UV-C sources 310 within the air disinfection unit may be adjusted by (1) adjusting the number of disinfection chambers 200 in the device, (2) adjusting the height of the disinfection chamber and thus the height of the helical air flow diverter, (3) adjusting the number of helical rungs in the helical air flow diverters, (4) varying the surface on the interior wall of the disinfection chamber with reflecting and/or irregular or crenulated walls to increase the light ray reflections; (5) adjusting the speed of the air flow through the device and/or (6) varying the diameter of the helical rungs to control the proximity of the UVC source to the pathogens.

UV Light Source.

The number, type, strength and the placement of the UV-C lights 62 in the disinfection chamber 52 will ensure that all microorganisms such as bacteria and viruses in the air flow passing through the disinfection chamber 52 will receive a sufficient UV-C dosage to kill any microorganisms in the air.

Likewise, the number, type, strength and the placement of the UV-C lights 310 in each disinfection chamber 200 will ensure that the bacteria and viruses in the air flow passing through the disinfection chamber 100 will receive a sufficient UV-C dosage to disinfect the air flowing through the device.

The UV-C light source 62 or 310 can be any type of UV-C light source, such as the UV-C tubes 64 shown in FIG. 5C or the UV-C light strips shown in FIG. 5A. UV-C light sources may include mercury lamps, fluorescent tubes, pulsed xenon lamps, excimer lamps, UV-C LEDs, and UV-C lasers. Once the UV-C light source is selected and the wattage or irradiance is known, the exposure time to achieve the desired dosage can be calculated and the appropriate time for the air path to spend passing through the disinfection chambers in close proximity to the UV-C lights can be determined. In fact, when more than one disinfection chamber is used, different UV-C light sources may be used in the different chambers. Different UV light sources may be selected for the different wavelengths that they produce, their different intensities, their different lifespans, the difference in their heat production, or for any other reason.

Figure 7:
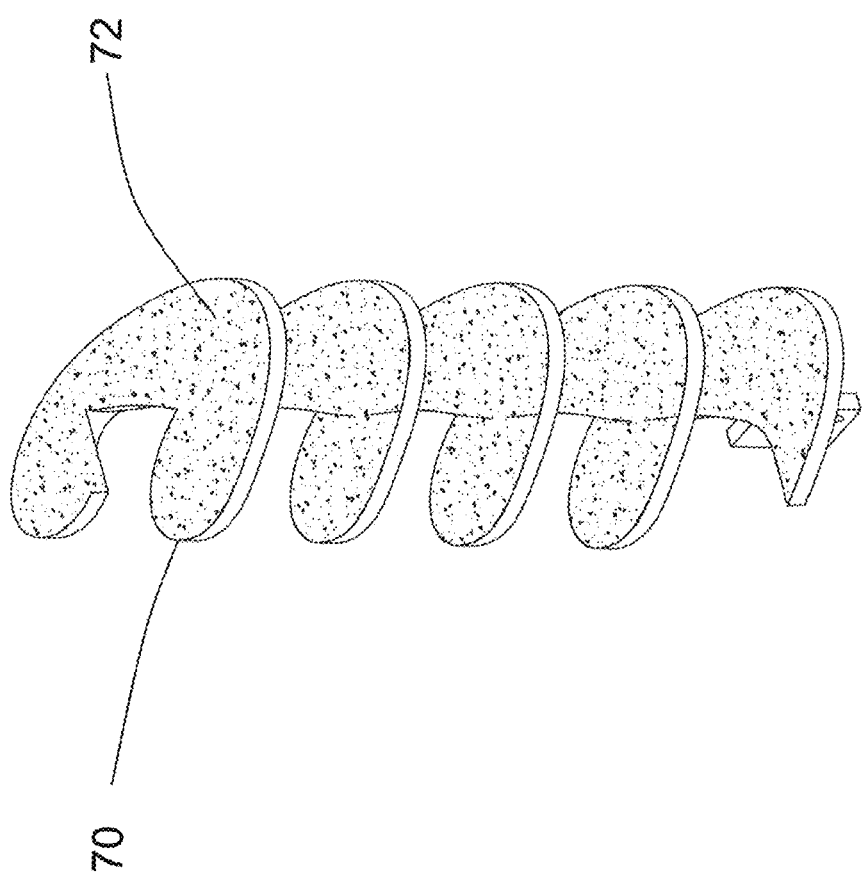
FIG. 7 shows an isometric view of the helical air flow diverter.

Helical Air Flow Diverter. One embodiment of the helical air flow diverter 70 is illustrated in FIG. 7. The helical air flow diverter provides a helical air flow passage within the disinfection chamber 52 or 200. Typically the helical air flow diverter fills most of the empty space in the disinfection chamber as seen in FIGS. 6A and 8C thereby creating an air flow path that circulates around each helical rung in a narrow space between the disinfection chamber wall 55 or 210 and the helical air flow diverter rungs. Thus as the air flows from the inlet 56 or 115 to the outlet 58 or 117, it circulates close to the UV-C light source(s) throughout the disinfection chamber(s). The particles including the pathogens in the air are driven very close to the UVC source on the chamber wall due to the centrifugal force.

The helical air flow diverter surface 72 may be optionally lined with reflective material and/or titanium dioxide with or without areas of irregular or crenulated surfaces as shown in FIG. 7. The helical air diverter found in the disinfection chamber may have any of a variety of variations: (a) variations in the number of rungs/discs of the diverter, where increases to the number of rungs will further interrupt a direct air flow path and increase the passage time; (b) variations in the air speed in a circular path around the rungs of the air diverter to vary the centrifugal force on the air to provide a closer contact between the pathogens and the UV-C source arranged around the periphery of the chambers; (c) increasing the diameter of the diverter discs, thereby reducing the space between the pathogens and the UV-C sources and the chamber walls; (d) making the chamber more lethal to the pathogens by coating the discs with titanium dioxide and increasing the reflectivity of the surface of the chambers between the UV-C light sources to ensure the continuous bombardment of the UV-C energy on the pathogens; and (e) making the reflecting surfaces irregular, to increase the UV-C scatter and make the UV-C sources even more effective.

The air disinfection unit 100 has multiple interconnected disinfection chambers 200 as seen in FIGS. 8B and 8C. In a similar manner as in the air disinfection unit 12, the helical air flow diverter 320 in each of the disinfection chambers 200 provides a helical air flow passage within each disinfection chamber as shown in FIG. 8D. Interlinking the disinfection chambers 200 to create a serpentine air flow path between adjacent disinfection chambers in addition to the helical air flow path within each disinfection chamber 200 (see FIG. 8D) provides increased exposure of the microorganisms in the airflow from the inlet 115 to the outlet 117 to UV-C or far UV-C light emitted by the ultraviolet light sources for an extended and optimal duration, with close contact due to the double serpentine course the air is forced to navigate. The air flow path and therefore the time and exposure of the air flow to the UV-C sources 310 within the device may be adjusted by (1) adjusting the number of disinfection chambers 200 in the device, (2) adjusting the height of the disinfection chamber and thus the height of the helical air flow diverter, (3) adjusting the number of helical rungs in helical air flow diverters, and/or (4) adjusting the speed of the air flow through the device.

Aerosolization of the Air Flow

The standardized pathogenic source is then aerosolized using an automated aerosol device, such as a Biaera Aero3G™, to produce air droplets of a known size containing a known viral count. The aerosolization is standardized to yield a known droplet size for specified air flow rates into and out of the disinfection device(s). Typically the air delivered to the disinfection device(s) will contain both aerosol droplets and diluter air. The aerosol droplets are programmed to be in the inhalable size range.

Air Mover

The air disinfection unit of the present invention relies on the air source to travel through the air disinfection unit to neuter or inactivate the microorganisms in the air. The air purification and disinfection system may utilize an air mover or air circulator, such as an air pump or a fan, in communication with the housing inlet or outlet to ensure a controlled rate of air flow through the air disinfection unit. The helical air path through each disinfection chamber will extend the time that the air is exposed to the UV-C light sources. The time the air spends in the disinfection chambers is further controlled by the speed of air movement through the chambers as controlled by the air mover. The speed of air movement through the system may be adjusted by adjusting the power level going to the air mover.

Figure 10A:
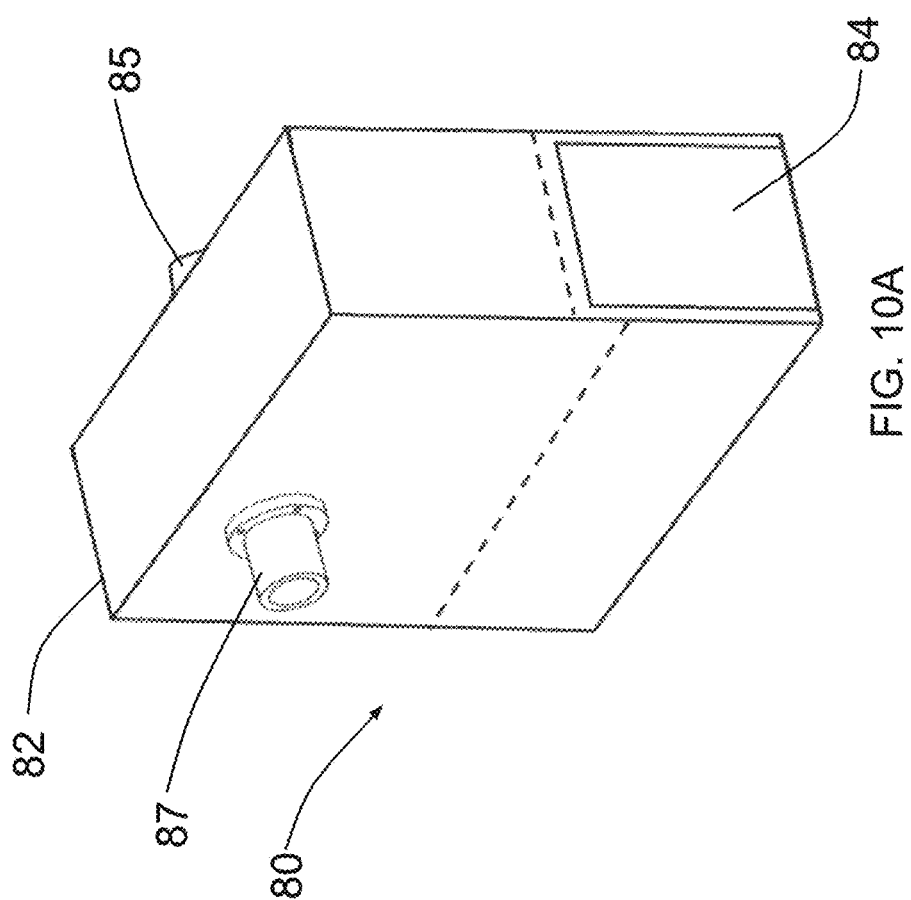
FIG. 10A illustrates one embodiment of an air mover.
Figure 10B:
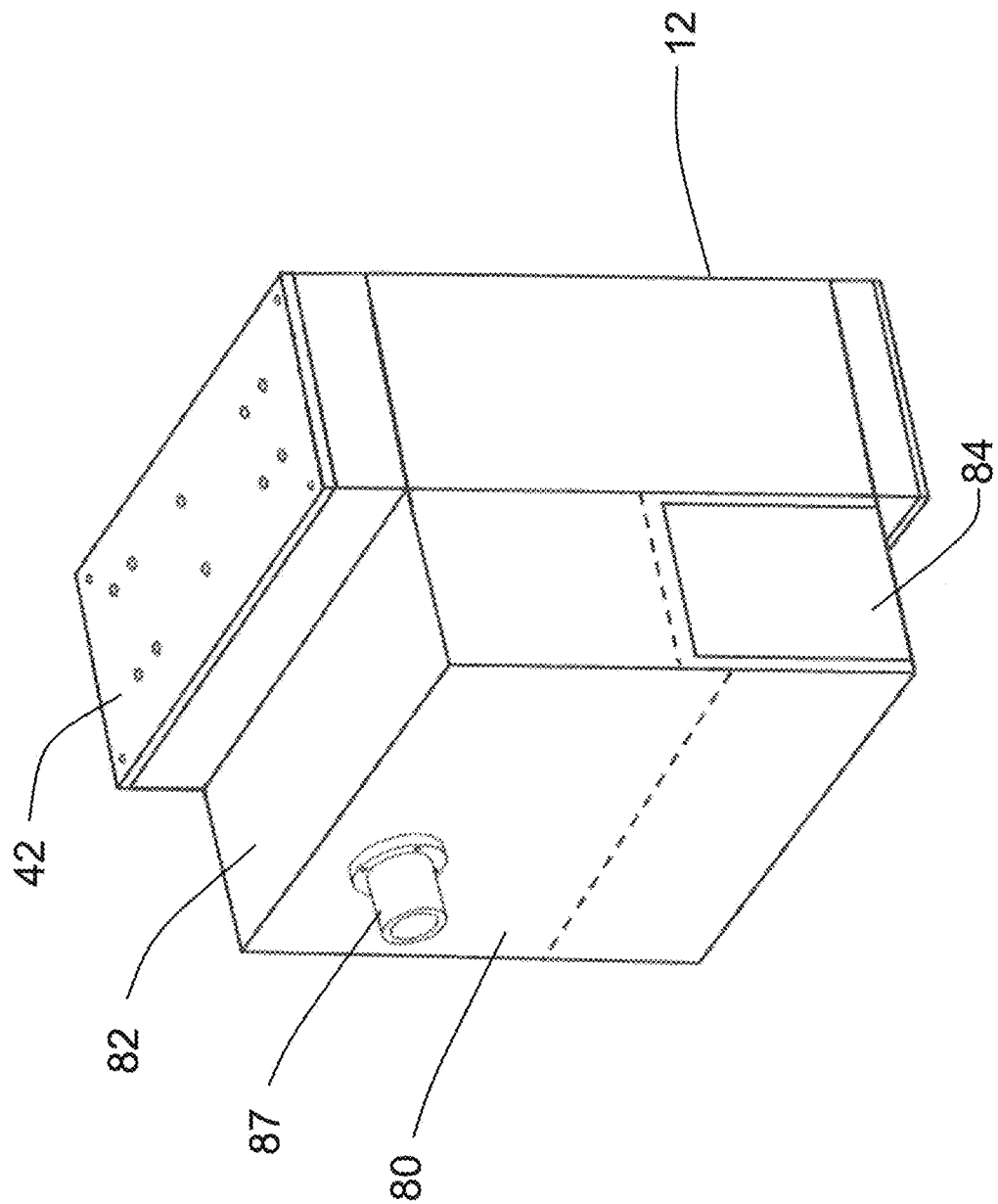
FIG. 10B illustrates one embodiment of an air disinfection unit interconnected with an air mover.

An air mover module 80 may be a standalone module, as illustrated in FIG. 10A, which may be interconnected to one or more air disinfection units via tubing or any other means. The air mover module 80 typically has an inlet 85, an outlet 87, an air mover 82 (such as a pump or fans), and a power supply 84 (such as a battery or a power cord). Alternatively, the air mover module may also be built into an air disinfection unit as shown in FIG. 10B.

The air mover controls the movement of the air through the air disinfection units. The air mover functions at different power levels that can be electronically controlled. By altering the power level of the air mover, the air circulation can be made faster or slower. The velocity of the air flow through the disinfection unit(s) will proportionately increase or decrease the dosage of UV-C encountered by any pathogen in the air flow through the disinfection unit(s).

Quantitating the Inactivation of a Pathogen by UV-C Controlled Dosage.

The UV-C air disinfection unit described above is a reliable means of delivering a set dosage of UV-C to a pathogen in an air supply that passes through the unit. The dosage can be varied by controlling the intensity of UV-C put out by the UV-C source(s), the number and position of the UV-C sources, the number of disinfection units and/or the number of disinfection chambers per disinfection unit. The dosage can also be varied by controlling the exposure time by varying the air flow velocity through the disinfection unit(s) or controlling the length of the air stream pathway through the unit. Examples of other variations include:

varying the strength of the UV-C sources, varying the proximity of the microorganisms in the air flow to the UV-C sources, varying the distance traveled by the air stream, and varying the time and proximity that the air steam is exposed to the UV-C light sources in the disinfection chambers 200 within air disinfection module 100.

Quantitating the Damage to a Pathogen.

Aerosolized samples of a standardized virulent pathogenic source will be collected before and after UV-C treatment in the disinfection device(s). Generally UV radiation will destroy the genetic material of the pathogen (i.e. DNA or RNA) before it will destroy any other molecules in the pathogen. A neutered pathogen is defined herein as a pathogen with its genetic material (i.e., its RNA or DNA) destroyed so that it cannot reproduce and yet has some or all of its membrane or structural proteins intact. For instance, a ribonucleic virus can be neutered by destruction of its RNA using UV-C in a dose related manner. Using a minimal UV-C dosage for destroying its genetic material allows the virus to retain its morphology and the structural integrity of its proteins. A vaccine derived from an intact neutered virus can generate antibodies to various antigenic regions available in one or more of the viral proteins.

Figure 11:
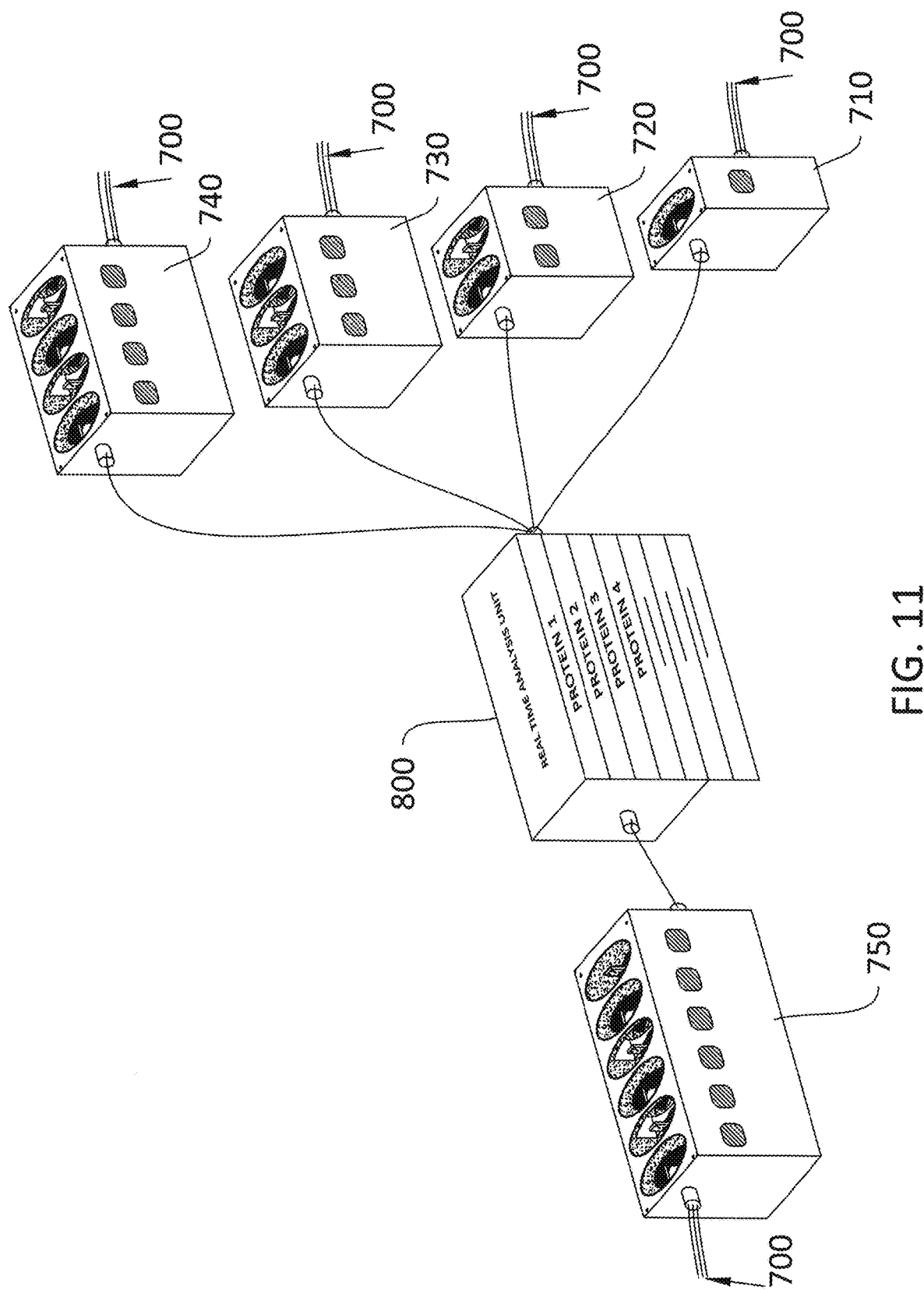
FIG. 11 is a perspective view of one embodiment of a system for titrating a dose-related damage to a pathogen.

Using the SARS-COV-2 virus as an example, aerosolized samples collected before and after they are subjected to a set dosage of UV-C radiation will be analyzed to compare the integrity of the samples' RNA and proteins to the known structure of the virus' known RNA and capsid proteins using standardized laboratory techniques such as 2D gel electrophoresis. One embodiment of this process is illustrated in FIG. 11, where an aerosolized standardized SARS-COV-2 viral source 700 is separately sent through a variety of disinfection devices 710, 720, 730, 740, and 750 that vary in the number of disinfection chambers within the devices. Increases in the number of disinfectant chambers will increase the dosage of UV-C delivered to the viral source. Samples from each disinfection unit will be collected by an automatic sampling apparatus 800 and analyzed for the integrity of the various viral components such as its RNA and proteins.

Numerous samples of the aerosolized standardized virulent pathogenic source will be subjected to incremental increases in UV-C dosages. With each incremental dosage increase the UV-C treated pathogenic source will be collected and analyzed for any damage to the genetic material and/or proteins of the untreated pathogenic source. Thus, any damage to the genetic material and/or proteins of the pathogenic source can be correlated to increases in the UV-C dosage used to treat the pathogenic source. For example, any damage to the genetic material and/or proteins of a standardized SARS-COV-2 source can be correlated to increases in the UV-C dosage used to treat the SARS-COV-2 virus. This information can be used to devise a method of neutering the COVID-19 virus without destroying its structure, including the nucleocapsid protein or its envelope proteins (the M protein, E protein and S protein). If the S protein retains its integrity after UV-C treatment, then it will continue to be able to engage SARS-COV-2 ACE2 receptors and competitively inhibit the untreated virus's ability to engage the same ACE2 receptors.

Other embodiments will vary the UV-C dosage given to an aerosolized standardized SARS-COV-2 viral source 700 by sending the viral source through a series of disinfection devices that vary in the number or type of their UV-C sources and/or disinfection chambers, or by sending the viral source through the disinfection device(s) at different velocities or flow rates. The dosage of UV-C delivered to the viral source is calculated and the degree of damage to the virus is quantified from samples collected by an automatic sampling apparatus 800 and analyzed for the integrity of the various viral components such as its genetic material (RNA or DNA) and its proteins.

Vaccine Production and Administration

Polyvalent Vaccines. The present invention includes a process for developing neutered whole pathogen vaccines involving the destruction of the RNA or DNA of the pathogen by using germicidal UV-C radiation. One embodiment of the present invention is a process for developing neutered whole viral vaccines that utilize the destruction of the RNA or DNA of the virus using germicidal UVC (or UV-C) radiation. For instance, the SARS-COV-2 virus can be neutered by destruction of its RNA using UV-C in a dose related manner. This allows the virus to retain its morphology and the structural integrity of its envelope proteins. To date the major SARS-COV-2 vaccines have been prepared to create antibodies to one or more portions of the S protein. However, the S protein has multiple domains. For example, if the vaccine is made only against the Receptor Binding Domain (RBD) of the S protein, the antibodies produced are only against one or two peptide portions of the S protein. As the virus continues to mutate, one or more of these mutations will eventually overcome this RBD vaccine.

Viruses rapidly reproduce in infected cells and often at least a few of the released virus particles will have mutated. Over time some of these mutations may be able to evade the antibodies made to an attenuated virus or to a portion of a protein used as an antigen in a vaccine. For example, SARS-COV-2 is an RNA virus. Typically, the SARS-COV-2 virus will try to evade the antibodies produced by a vaccine to one or more antigens used in producing the vaccine. However, the SARS-COV-2 has three envelope proteins and the nucleocapsid protein around the RNA. If each of these proteins generated one or more antibodies then it would be harder for the virus to mutate enough to avoid all of the antibodies produced. The mutation of the virus to evade all of the antibodies produced to a variety of proteins will be difficult. This is because mutation is sustained and propagated only through progeny. If the mutation does not generate progeny, that particular mutation is discarded. In time, the virus will continue to try and mutate, but will then have to stop. Thus, vaccine evasion by a multi-mutated virus will be significantly reduced.

A vaccine derived from an intact neutered virus can generate antibodies to various antigenic regions available in one or more of the viral envelope or capsid proteins providing a full spectrum of antigens capable of eliciting a full spectrum of antibodies. For example, SARS-COV-2 has several envelope proteins—the spike protein (S protein), the membrane protein, and the envelope protein in addition to the nucleocapsid protein; wherein each of these proteins can potentially independently elicit specific antibodies to one or more antigenic regions in each protein.

Another embodiment of the present invention includes a process for producing a vaccine to predictably destroyed architecture of the inactivated pathogen, such as a virus. The process comprises standardizing a virulent pathogenic source; titrating the degree of ultraviolet inactivation of the pathogenic source; preparing an inoculum, or vaccine, to produce or increase immunity to the inactivated pathogenic source.

A vaccine derived from an intact neutered virus can generate antibodies to various antigenic regions available in one or more of the viral proteins providing a full spectrum of antigens capable of eliciting a full spectrum of antibodies.

For example, SARS-COV-2 has several envelope proteins—the spike protein (S protein), the membrane protein, and the envelope protein, in addition to the nucleocapsid protein; wherein each of these proteins can potentially independently elicit specific antibodies to one or more of their antigenic regions. If antibodies are generated to antigenic regions of more than one protein, then a viral mutation to circumvent one particular antibody might remain unmutated while it tries to mutate against another antibody. For any mutation to prevail and propagate, it has to have successful progeny. If mutation does not produce progeny that particular mutation is usually discarded. In other words, not all mutations result in a new variant. In time, the virus will continue to try and mutate, but will then have to stop. Thus, vaccine evasion by the virus can be significantly reduced. A reduced rate of mutation will naturally occur through a reduced rate of infection. SARS-COV-2 virus cannot multiply or mutate in the air but must mutate in infected cells. By blocking the entry of the virus into our bodies, the rate of mutation is automatically eliminated or reduced. The polyvalent vaccine has a better chance to do this. With four types of antibodies to evade, the chances are exponentially lower than with just one type of antibody. This is like a burglar trying to unlock four locks on a door at the same time. With any luck, the burglar will keep locking and unlocking the four locks randomly and will never get all the four unlocked at the same time. The polyvalent vaccine can give similar challenge to the virus. Partial S protein antibodies are even easier to evade by mutation. Imagine S protein-lock has seven levers. The mutations have to cover all seven. If the antigen is only part of S protein, the antibody produced is only against a few of these seven levers. This makes the mutation much easier.

In the simplest form of UV-C damage to the SARS-COV-2 virus, only the RNA is damaged and the envelope (capsule) and all the four proteins are preserved. It is unlikely that all four proteins have the same threshold for destruction by UV-C. The same is true for the structure of the envelope itself. After determining the gradation of sensitivity for destruction of viral components by UV-C, one can predictably produce different levels of SARS-COV-2 damage such as RNA damage with all four proteins preserved, RNA and one protein damaged with three proteins preserved, RNA and two proteins damaged with two proteins preserved, and RNA and three proteins damaged with only one protein preserved. A vaccine can be produced from any one of these graded options and that vaccine can be tested for diverse antibody production and their risks and benefits. Thus, an educated selection can be made of which damaged virus should be included in the inoculum or vaccine. Theoretically, the first option with all four proteins preserved will have more advantages than the others.

The development of polyvalent neutered whole virus vaccine can be explained using SARS-COV-2 as an example. This virus has positive-sense, single strand, RNA combined with nucleoprotein as its core. This type III virus has an envelope made of two main proteins, the M (for membrane or matrix) and E (for envelope) and an "attack" protein projecting out and appropriately called the spike protein. By utilizing two-unit systems, to produce predictable, graded, optimal damage to the virus, it should be possible to produce four types of antigens. The lowest dose of UV-C can just neuter the SARS-COV-2 by denaturing the RNA without damaging the architecture of the virus or the four proteins. This product will have four potential antigens from the four preserved proteins for creating a broad-spectrum antibody reaction. By increasing the strength and duration of the UV-C and the proximity of the virus to the UV-C right inside the first chamber/unit, a second possible product will be a neutered virus with one damaged protein. It will not be difficult to measure the sensitivity of the four proteins to UV-C, and by using appropriate dose of UV-C the viral antigen can be with four proteins, three proteins, two proteins and just one protein.

Since the RNA is denatured in all four of these products, the resulting whole virus cannot be multiplied in any cell and is not infective. It is difficult to predict which of these four UV-C damaged viruses will make the optimal vaccine. This has to be determined with animal experiments and a determination of risks versus benefits. Common sense dictates that the neutered virus with four antibody-producing proteins will be the best vaccine. In this situation, the virus will have to create mutations against all antibodies at the same time to evade the vaccine. Mutations are "errors" produced during virus multiplications in the cells (accidental evolutionary, random or whatever) but not calculated or intentional. The more viruses in circulation the more chance for mutations. Such mutations take place in each infected person through each virus multiplication cycle. At the peak of COVID-19, the estimated number of mutations generated daily in the world was about 100,000 to 1 million.

A neutered SARS-COV-2 virus is like a defanged cobra. A defanged cobra can crawl into crevices and get into a house, but it cannot hurt the inhabitants without its teeth. Likewise, the neutered SARS-COV-2 virus, that retains its morphology, will invade human cells through the same ACE2 entrance gates. Then, the neutered SARS-COV-2 virus would die with no progeny. Additionally, the undamaged proteins released by the dead virus can provide foreign antigens that the body can generate antibodies against. These antibodies can then attack and defeat any future active virus invasions. The multiple antibodies produced against different components of the virus can react with the virus and negate its ability to reproduce and cause illness. Furthermore, the virus will struggle to overcome these multiple protein antibodies. Using a specialized pathogen-killing or pathogen-taming system, vaccines of these four grades can be created. The predictable graded destruction of the pathogens will facilitate the development of reliable and optimal vaccines.

A neutered, inactivated live virus vaccine provides the benefits of live vaccines without the risk of the individual getting infected. Attenuated live vaccines tend not to infect the individual; however, the live vaccine can sometimes misbehave and thereby infect an individual. The neutered SARS-COV-2 vaccine is better than inactivated whole virus vaccines as it does not have any side effects from the agents used to inactivate the virus. Also, the virus and its capsid or envelope proteins are not mutilated in the process of neutering it, unlike in the process of inactivating the virus using other methods. The UV-C treated neutered SARS-COV-2 virus behaves like the whole virus in its antigenic potential without any side effects and without causing any infection by accident.

It is a known fact that most of the human pathogens are transmitted to humans from the original sources from birds, bats, chimpanzees etc. One of the methods to reduce human infection is by controlling the infection in the animals, birds, bats etc. by vaccinating them and isolating the infected ones this may be an alternative to sacrificing a large population of cattle, chicken etc. and can save lives as well as money.

Figure 12:
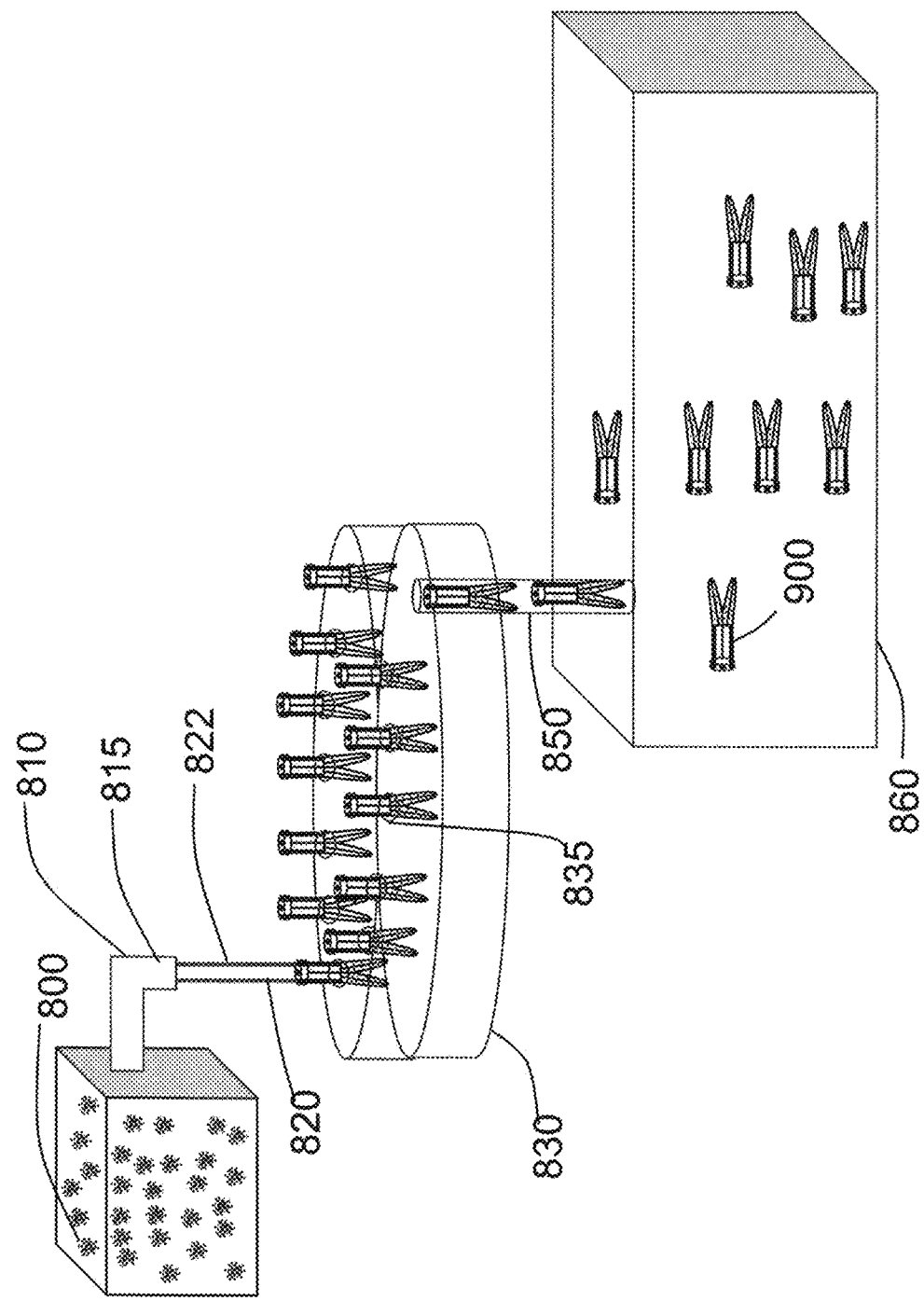
FIG. 12 illustrates one embodiment of a loading device.

Inoculum. A measured amount of a quantifiably damaged pathogen may be prepared as an inoculum or vaccine 800, with or without an adjuvant, and loaded into specialized containers for the administration of the vaccine as shown in FIG. 12. Various embodiments include storing multiple vaccine doses in the specialized container or each container may optionally represent a single vaccine dose. One embodiment of a specialized container is an inhalation pump 900.

The vaccine can be administered by injecting a vaccine dose using a regular syringe method, preferably one-half dose into each nostril. Another embodiment includes selecting a neutered whole virus, such as the SARS-COV-2 virus, preparing an inoculum from the neutered virus, and aliquoting the inoculum into inhalation pumps as described below.

Loading Device. The specified dose of inoculum is injected into the inhalation pumps 900 using an inoculum loading device 810. The inoculum loading device 810 has an injection arm 815 that has two needle loading lines 820, 822. The loading device 810 has a revolving platform 830 containing a circular ring of openings 835. Each opening 835 is configured to hold an inhalation pump 900 bottom-side up. Each inhalation pump 900 has two fill tubes 912, 914 on opposed sides of the bottom compartments of the inhalation pump. The two loading lines 820, 822 fit securely into the two inhalation pump fill lines 912, 914.

As the platform 830 rotates, the loading device injects a set dosage of vaccine through each loading line 820, 822 into the two inhalation pump fill lines 912, 914 and up into the bore 935 of the two top compartments 909. Once the two top compartments 909 are filled with the vaccine, the inhalation pump fill lines 912, 914 are sealed. The sealed vaccine-filled inhalation pumps are sent through a platform outlet 850 into a refrigerated storage unit 860 to be stored until needed.

Inhalation Pumps. According to an embodiment, the vaccine derived from a neutered whole virus can be applied through a nasal inhalation process. An inhalable vaccine simplifies the application process and can greatly improve the acceptance of the vaccine by the general population. Alternately the vaccine can be administered by mouth or parenterally. Administering the vaccine through inhalation has another unique advantage. Assuming that the virus is just neutered and its architecture is not destroyed, the remaining "whole virus" will act like a "pseudo virus" with its intact spike proteins. These intact spikes will hopefully engage the ACE2 receptors on the COVID-19 landing ports in the nostrils, pharynx and upper respiratory tract without causing the infection or virus multiplication inside the cell. When the true virus enters the scene, it cannot find any gates to enter the cell and is lost without a home. This type of competitive inhibition is possible uniquely with the neutered inhalation form of the vaccine invented through this technique. No vaccine in the history has been able to accomplish this phenomenon.

The inhalation pump 900, as illustrated in FIGS. 13A and 13B, has a first half 905 and a second half 907. Each half has a bottom compartment 908 and a top compartment 909. In one embodiment each of the two top compartments 909 are shaped like a nose cannula. Each top compartment has a bore 935 that is filled with vaccine. Optionally each of the nose cannulas may curve backwards about 40 to 60 degrees. This curvature allows the cannula to easily enter the patient's nasal passages and allows the inhalation pump to pump the vaccine into the posterior ⅔ of each nasal passage. The right cannula is used to pump vaccine into the left nostril and the left cannula is used to pump vaccine into the right nostril. The vaccine is loaded into the two top compartments through tubes 912, 914 that run along the sides of the two bottom compartments as described above. The two nose cannulas have a breakable cap 930 at their tips. Once the cap 930 is removed, the vaccine can be released.

Some embodiments of the bottom compartments 908 are tubular with an inner bore 928 filled with compressed neutral air. The top of the inner bore is sealed with a breakable barrier 926 between the interior of the top compartment containing the vaccine and the bottom compartment 908 containing the compressed air. The bottom end of the inner bore is sealed with a movable end 903 similar to the simple reciprocating end of a syringe plunger. The end 903 is attached to a plunger 902 that fits tightly within the inner bore of the cylindrical bottom compartment 908.

To administer the vaccine, the end cap 930 is removed from both of the top compartments and a plunger 902 is pushed upwards through the inner bore 928 of the two bottom compartments toward the top compartments 909. The compressed air in the inner bore 928 of the two bottom compartments becomes even more compressed and the increased pressure breaks the barrier 926 and forces the vaccine into the patient's nostril.

The compressed air in the bottom compartment will ensure the complete emptying of vaccine from the top compartment into the patient's nostril. Inhalation pumps 900 can be used to introduce the inoculum or vaccine into the rear two thirds of the nasal passage. Nasal vaccinations generally require a minimal volume of the vaccine to be effective. The inhalation pump 900 with its high vaccine deliverance into the patient's nostrils will reduce the volume of vaccine required for an active immune response.

Advocates of inhalation vaccines have highlighted that they promote both a mucosal immune response in addition to a systemic immune response. A nasal vaccination is easier to dispense and more likely to be accepted. Intranasal vaccinations are not invasive and cause patients minimal discomfort. Because many people are afraid of needles and injections, a nasal vaccination may increase patient acceptance and compliance.

SARS-COV-2 virus enters the body through the upper airways and spreads to the rest of the body. More specifically, the rear two thirds of the nasal passage is known as the landing place for this virus. This is why one swabs the rear portion of their nasal passage for a proper diagnosis of this virus. By providing a vaccine that can be inhaled and deposited in the rear two thirds of the nasal passage, the attack on the virus is focused at its first landing place and will be more effective. This will also ensure that the neutered and artificially created "pseudo virus" will engage all the ACE2 entry points on the host cells making the true virus particles lost in the wilderness with no ACE2 entry points in the upper respiratory tract.

COVID-19 researchers have attempted to improve the systemic immune response and the mucosal immune response. Advocates of inhalation subunit vaccines have highlighted this as an additional benefit of inhalation vaccines. Promoting both a mucosal immune response and a systemic immune response may be achieved by a total viral protein vaccine and will perform better than the subunit vaccines currently undergoing clinical trials.

According to an embodiment, the vaccine derived from a neutered whole virus can be applied through a nasal inhalation process. An inhalable vaccine simplifies the application process and can greatly improve the acceptance of the vaccine by the general population.

In one or more embodiments, a formal storage facility can be created to store the vaccine grade pathogens that can be dispensed into inhalation units, parenteral units. In other embodiments, one or more or facilities can be set up to make liquid capsules, tablets or other forms for oral administration.

In yet another embodiment, a conveyer belt like arrangement can be devised to load the vaccine into the inhalation units, parenteral administration units or the bottles to contain the oral route units.

While the foregoing describes various embodiments of the invention, additional embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

I claim:

1. A method for producing an immunogenic composition comprising:
   (a) neutering an intact pathogenic source, wherein neutering the pathogenic source involves:
      destroying the genetic material of the pathogenic source by varying a dosage and/or a wavelength of UV-C radiation such that the pathogenic source is unable to reproduce or cause infection while leaving intact at least some or all of its membrane or structural proteins as antigens; and
   (b) aliquoting the neutered pathogenic source into containers,
   wherein the pathogenic source is neutered in a disinfectant unit comprising:
   a housing that is opaque to UV-C radiation/light; and
   a chamber enclosed within the housing, wherein the chamber comprises:
      (i) a chamber wall that is transparent to UV-C light;
      (ii) a chamber inlet;
      (iii) a chamber outlet;
      (iv) a centralized inner bore having an interior chamber surface facing the inner bore;
      (v) one or more UV-C light source positioned adjacent the interior surface; and
      (vi) a helical air flow diverter centralized within the inner bore proximal the one or more UV-C light sources, wherein the helical air flow diverter comprises one or more rungs, wherein the helical airflow diverter creates a centrifugal force and a helical path for the airflow pathway as the airflow pathway proceeds from the housing inlet to the housing outlet, and
   wherein varying the dosage and wavelength of the UV-C radiation involves:
   (A) controlling one or more of the following parameters:
      (i) intensity of UV-C emitted by the one or more UV-C light sources;
      (ii) number, type and position of the one or more UV-C light sources; and
      (iii) number of disinfectant units and/or number of chambers per disinfectant unit; and/or
   (B) controlling the exposure time of the pathogenic source to the UV-C by adjusting or varying one or more of the following parameters:
      (i) height of the chambers per disinfectant unit to thereby increase the height of the helical air flow diverter,
      (ii) number of helical rungs,
      (iii) a surface on the chamber wall with reflecting and/or irregular or crenulated walls to increase light ray reflections;
      (iv) speed of the air flow through the device,
      (v) a diameter of the helical rungs to control the proximity of the UV-C light source to the pathogens,
      (vi) air flow velocity through the disinfectant unit(s); and
      (vii) length of an air stream pathway through the disinfectant unit.

2. The method as claimed in claim 1, wherein the pathogenic source is a virus.

3. The method as claimed in claim 1, wherein the pathogenic source is a SARS-COV-2 virus.

4. The method as claimed in claim 1, wherein an aliquot of the neutered pathogenic source is injected into an inhalation pump.

5. The method as claimed in claim 4, wherein the aliquot of the neutered pathogenic source is injected into a first and a second upper compartment of the inhalation pump.

6. The method as claimed in claim 1, wherein an aliquot of the neutered pathogenic source is injected into a syringe.

7. The method as claimed in claim 4, wherein the inhalation pump comprises:
   (a) a first half and a second half, wherein each half has a top compartment and an adjoining bottom compartment;
   (b) a fill line associated with each half, the fill line having a septum on a bottom end and a top end that enters a central bore in the top compartment;
   (c) each bottom compartment is filled with compressed air and has a moveable bottom end opposite to the adjoined top compartment; and
   (d) each top compartment has a releasable cap at a top end opposite to the adjoined bottom compartment.

8. The method as claimed in claim 1, further comprising administering an aliquot of the neutered pathogenic source to a patient by an intramuscular, subcutaneous, or intravenous injection.

9. The method as claimed in claim 1, further comprising orally administering an aliquot of the neutered pathogenic source to a patient.

10. The method as claimed in claim 9, wherein an aliquot of the neutered pathogenic source is administered in a tablet or a liquid form.

11. The method as claimed in claim 1, further comprising administering an aliquot of the neutered pathogenic source to a patient through an inhalation, injection, or oral route.

12. The method as claimed in claim 7, wherein the moveable bottom end is attachable to a syringe.

13. The method as claimed in claim 1, wherein the immunogenic composition comprises a vaccine for promoting an immune response.

* * * * *